US010052467B2

(12) United States Patent
Bansal et al.

(10) Patent No.: US 10,052,467 B2
(45) Date of Patent: Aug. 21, 2018

(54) APPLICATOR FOR APPLYING A FLUID TO A SURFACE

(71) Applicant: Amneal Pharmaceuticals LLC, Bridgewater, NJ (US)

(72) Inventors: Padam Bansal, Bridgewater, NJ (US); Hardik Patel, Edison, NJ (US); David R. Schiff, Highland Park, NJ (US); Jason Zerweck, Media, PA (US)

(73) Assignee: Amneal Pharmaceuticals LLC, Bridgewater, NJ (US)

( * ) Notice: Subject to any disclaimer, the term of this patent is extended or adjusted under 35 U.S.C. 154(b) by 363 days.

(21) Appl. No.: 14/956,507

(22) Filed: Dec. 2, 2015

(65) Prior Publication Data

US 2016/0082237 A1    Mar. 24, 2016

Related U.S. Application Data

(63) Continuation of application No. 14/100,817, filed on Dec. 9, 2013, now Pat. No. 9,227,044.

(51) Int. Cl.
*A61M 35/00* (2006.01)
*A61K 31/568* (2006.01)
*A61K 9/00* (2006.01)

(52) U.S. Cl.
CPC ......... *A61M 35/003* (2013.01); *A61K 9/0014* (2013.01); *A61K 31/568* (2013.01)

(58) Field of Classification Search
CPC ............................. A61M 35/00; A61M 35/003
(Continued)

(56) References Cited

U.S. PATENT DOCUMENTS

| 4,726,700 A | 2/1988 | Gray |
| 5,904,151 A | 5/1999 | Gueret |

(Continued)

FOREIGN PATENT DOCUMENTS

| WO | WO-99/64313 | 12/1999 |
| WO | 2006/005135 A1 | 1/2006 |
| WO | WO-2013/000778 | 1/2013 |

OTHER PUBLICATIONS

Extended European Search Report in Appln. No. 14868970.6 dated Aug. 2, 2017, 8 pages.
(Continued)

*Primary Examiner* — Susan Su
(74) *Attorney, Agent, or Firm* — Servilla Whitney LLC

(57) ABSTRACT

An applicator for applying a fluid to a surface is provided, the applicator comprising a support comprising an upper outer surface and a lower holding surface; a flexible membrane comprising a central opening, an inner wall comprising a lower end and an upper end, an outer wall at least partially surrounding the upper outer surface of the support, the outer wall comprising a lower end and an upper end, and an upper folded wall connecting the upper ends of the inner wall and outer wall; and a membrane holder for fixedly securing the lower end of the inner wall of the flexible membrane to the upper outer surface of the support; wherein the upper surface of the membrane holder and the inner wall of the flexible membrane define a reservoir for holding a fluid, and wherein the lower end of the outer wall of the flexible membrane is free to move axially relative to the upper outer surface of the support when pressure is applied to the upper folded wall of the flexible membrane. In an embodiment, the applicator has particular utility for applying a topical or transdermal testosterone composition to the skin of a patient in need of testosterone replacement therapy.

19 Claims, 40 Drawing Sheets

(58) Field of Classification Search
USPC .................................... 604/289, 290, 310
See application file for complete search history.

(56) References Cited

U.S. PATENT DOCUMENTS

| | | | |
|---|---|---|---|
| 6,299,900 B1 | 10/2001 | Reed et al. | |
| 6,309,128 B1 | 10/2001 | Griebel et al. | |
| 6,773,187 B2 | 8/2004 | Gueret | |
| 6,818,226 B2 | 11/2004 | Reed et al. | |
| 6,923,983 B2 | 8/2005 | Morgan et al. | |
| 6,945,723 B1 | 9/2005 | Gueret | |
| 6,981,814 B2 | 1/2006 | Geardino et al. | |
| 7,381,005 B2 | 6/2008 | Altonen et al. | |
| 7,927,034 B2 | 4/2011 | Staniforth et al. | |
| 8,071,075 B2 | 12/2011 | Reed et al. | |
| 8,177,449 B2 * | 5/2012 | Bayly | A45D 34/04 401/11 |
| 8,419,307 B2 | 4/2013 | Bayly et al. | |
| 8,435,944 B2 | 5/2013 | Dipietro et al. | |
| 8,469,621 B2 | 6/2013 | Zukowski et al. | |
| 9,827,407 B2 * | 11/2017 | Carrara | A61M 35/003 |
| 2004/0047674 A1 | 3/2004 | Geardino et al. | |
| 2005/0054991 A1 | 3/2005 | Tobyn et al. | |
| 2007/0189841 A1 | 8/2007 | Gueret | |
| 2007/0206987 A1 * | 9/2007 | Phipps | A61M 35/003 401/175 |
| 2007/0293842 A1 | 12/2007 | Knight et al. | |
| 2010/0217176 A1 | 8/2010 | Carrara et al. | |
| 2011/0110702 A1 * | 5/2011 | Song | A45D 34/04 401/262 |
| 2012/0074176 A1 | 3/2012 | Sullivan et al. | |
| 2012/0220959 A1 | 8/2012 | Bayly et al. | |
| 2012/0259277 A1 | 10/2012 | Shay et al. | |
| 2014/0221945 A1 | 8/2014 | Dos Santos et al. | |
| 2014/0270897 A1 | 9/2014 | Laurusonis | |
| 2015/0045702 A1 | 2/2015 | Lin | |

OTHER PUBLICATIONS

Highlights of Prescribing Information for Axiron (testerone) topical solution, for topical use CIII, 17 pages.
PCT International Search Report and Written Opinion in PCT/US2014/068296, dated Mar. 20, 2015, 14 pages.
TM Reg. No. 4,277,418, Registered Jan. 15, 2013, 2 pages.
International Preliminary Report of Patentability in PCT/US2014/068296, dated Jun. 23, 2016, 9 pgs.

* cited by examiner

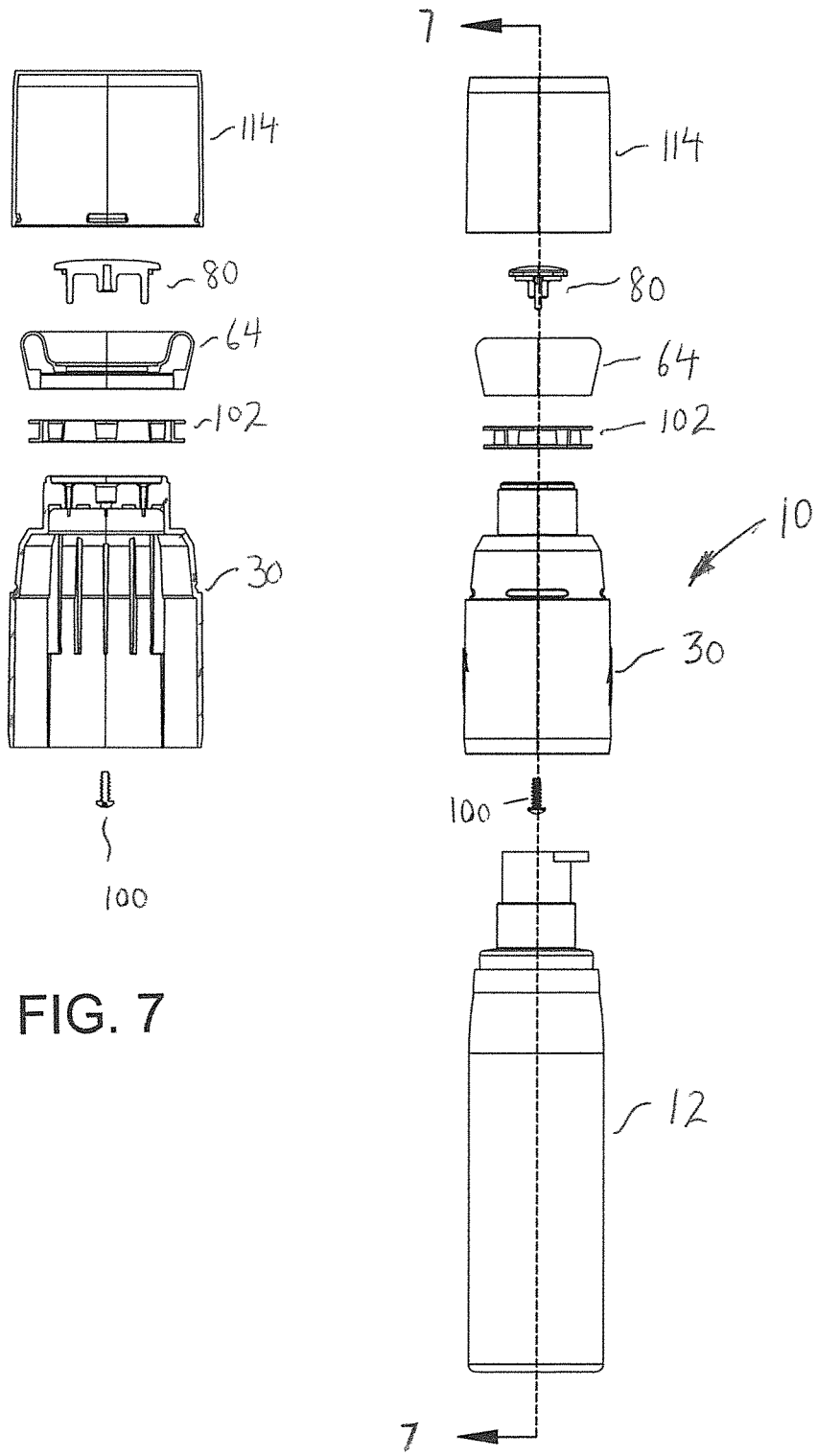

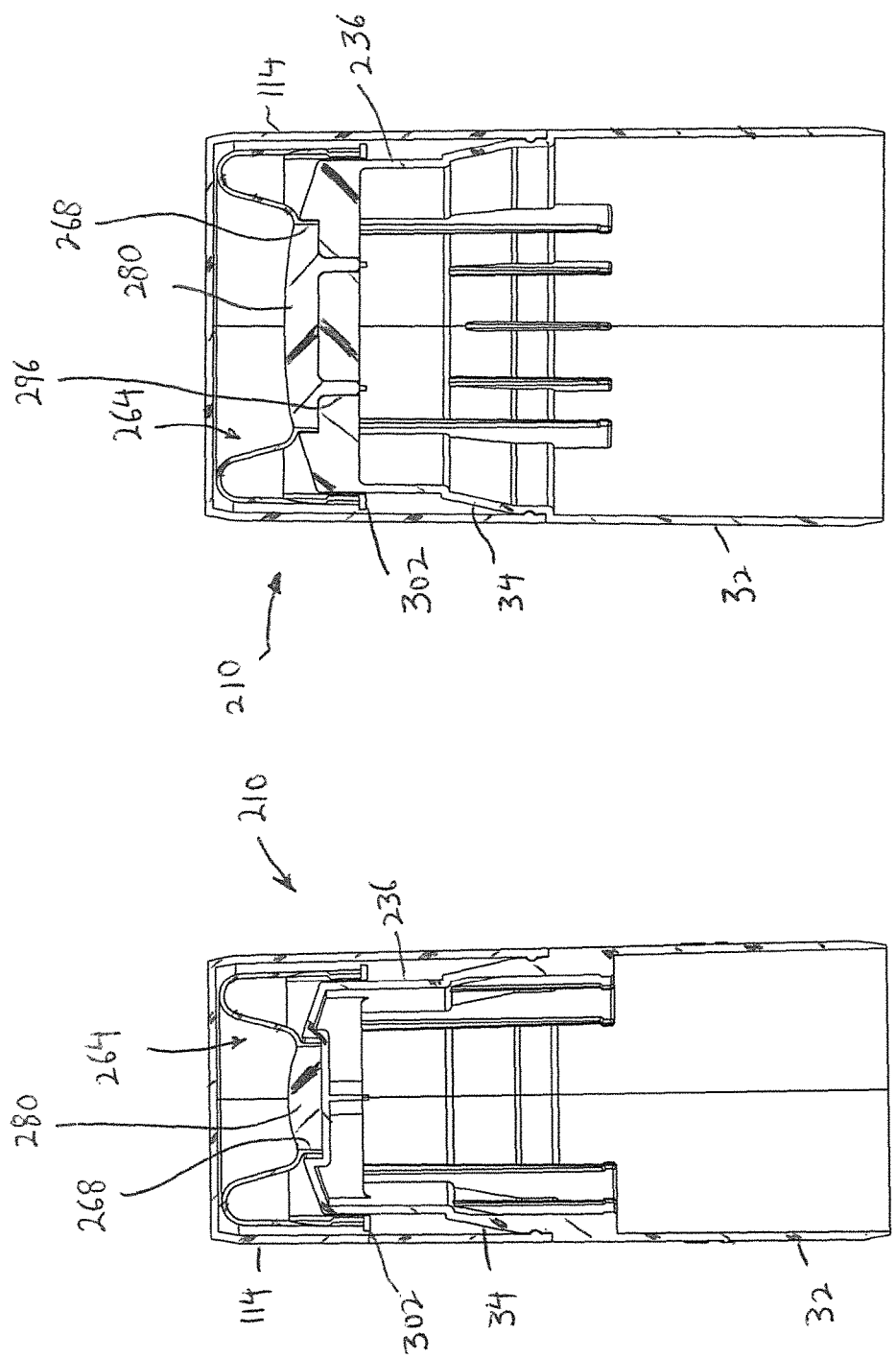

APPLICATOR FOR APPLYING A FLUID TO A SURFACE

CROSS-REFERENCE TO RELATED APPLICATIONS

This application is a continuation of and claims the benefit of priority of pending U.S. application Ser. No. 14/100,817, filed on Dec. 9, 2013. The foregoing application and all documents cited therein are hereby incorporated herein by reference in their entireties.

BACKGROUND OF THE INVENTION

The present invention relates to an applicator for applying a fluid to a surface. In embodiments, the applicator is useful for applying a medicament-containing fluid to the skin. In particular embodiments, the applicator is useful for applying a topical or transdermal testosterone composition to the skin of a patient in need of testosterone replacement therapy.

It is known from U.S. Pat. No. 8,177,449 to Bayly et al. to provide an implement for applying a volume of liquid containing testosterone to an underarm or axilla skin surface. This implement includes a cylindrical rigid support or handle on which a resiliently deformable thin flexible membrane is mounted. The membrane has a generally circular shape, with an inner circular area or base in contact with, but not secured to, the upper surface of the cylindrical rigid support. The membrane extends upwardly away from the circumference of the fixed inner circular area and is folded over to create an upper folded edge. The membrane then extends back down towards the rigid support, with the outer circumference of the membrane forming a lower outer edge which is fixed in position to the rigid support. With this structure, the secured inner circular area or base, and the upstanding wall, form a reservoir. In operation, a volume of liquid is pumped into the reservoir. The upper folded edge the membrane is then rubbed over the skin surface to which the liquid is to be applied, whereby the upper folded edge spreads the liquid over this skin surface.

However, it has been found that, with the implementation of this patent, the upper folded edge of the membrane tends to deform rather than roll over the skin surface. As a result of this deformation, a seal is difficult to maintain, with some leakage of the liquid from between the implement and the skin surface. In addition, because of this action, underarm hairs tend to be pulled, causing discomfort to the person.

SUMMARY OF THE INVENTION

In aspects, the present invention provides an applicator that overcomes the aforementioned problems.

In one aspect, the present invention provides an applicator for applying a fluid to a surface, the applicator comprising:
1) a support comprising an upper outer surface and a lower holding surface;
2) a flexible membrane comprising:
a central opening,
an inner wall comprising a lower end and an upper end,
an outer wall at least partially surrounding the upper outer surface of the support, the outer wall comprising a lower end and an upper end, and
an upper folded wall connecting the upper ends of the inner wall and outer wall; and
3) a membrane holder for fixedly securing the lower end of the inner wall of the flexible membrane to the upper outer surface of the support; wherein the upper surface of the membrane holder and the inner wall of the flexible membrane define a reservoir for holding a fluid, and wherein the lower end of the outer wall of the flexible membrane is free to move axially relative to the upper outer surface of the support when pressure is applied to the upper folded wall of the flexible membrane.

In another aspect, the present invention provides a kit comprising the disclosed applicator, a dispenser bottle containing a fluid, and a cap adapted to engage the support and cover the flexible membrane.

In another aspect, the present invention provides a method of applying topical or transdermal testosterone composition to the skin of a human in need thereof, the method comprising providing the disclosed applicator, placing the topical or transdermal testosterone composition in the reservoir of the applicator, and applying the topical or transdermal testosterone composition from the reservoir to the skin.

Various embodiments of aspects of the invention are disclosed below. The above and other features of the invention will become readily apparent from the following detailed description thereof which is to be read in connection with the accompanying drawings.

BRIEF DESCRIPTION OF THE DRAWINGS

FIG. 6 is an exploded, side elevational view of the applicator and dispenser bottle;

FIG. 7 is a cross-sectional view of the applicator of FIG. 6, taken along line 7-7 thereof;

FIG. 40 is an enlarged cross-sectional view of the applicator of FIG. 37 in assembled form;

FIG. 41 is an enlarged cross-sectional view of the applicator of FIG. 39 in assembled form;

DETAILED DESCRIPTION

Figure 1:
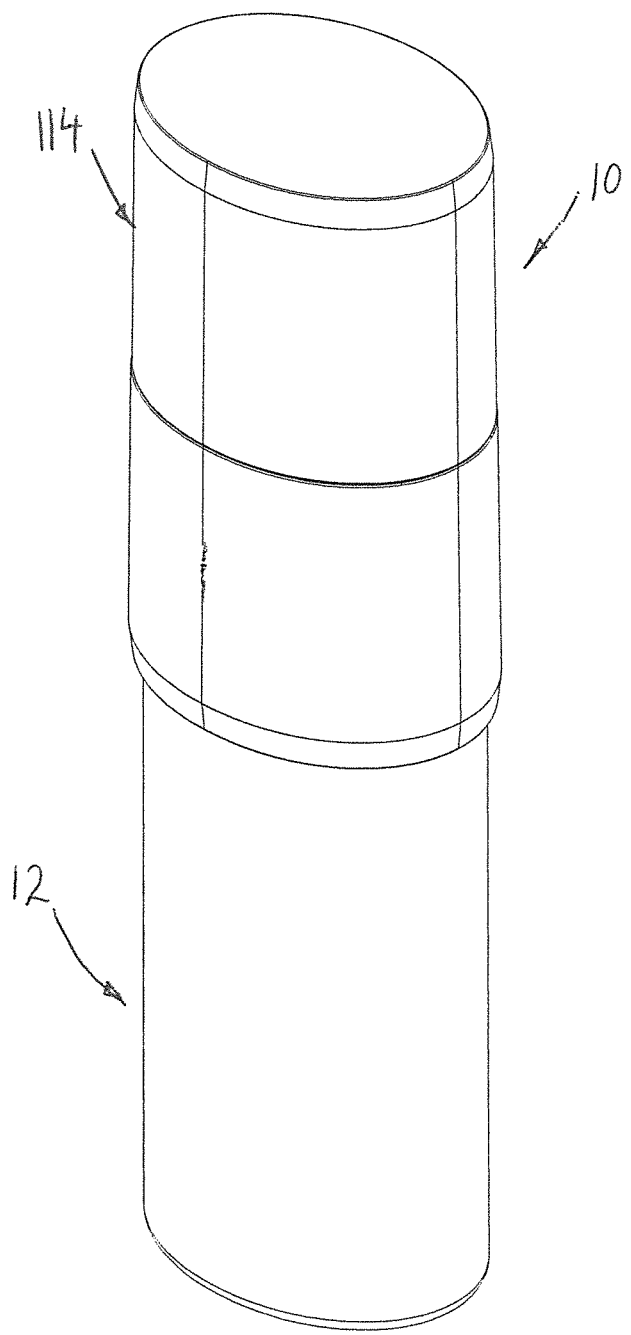
FIG. 1 is a perspective view of an applicator according to the present invention, mounted on a dispenser bottle.
Figure 2:
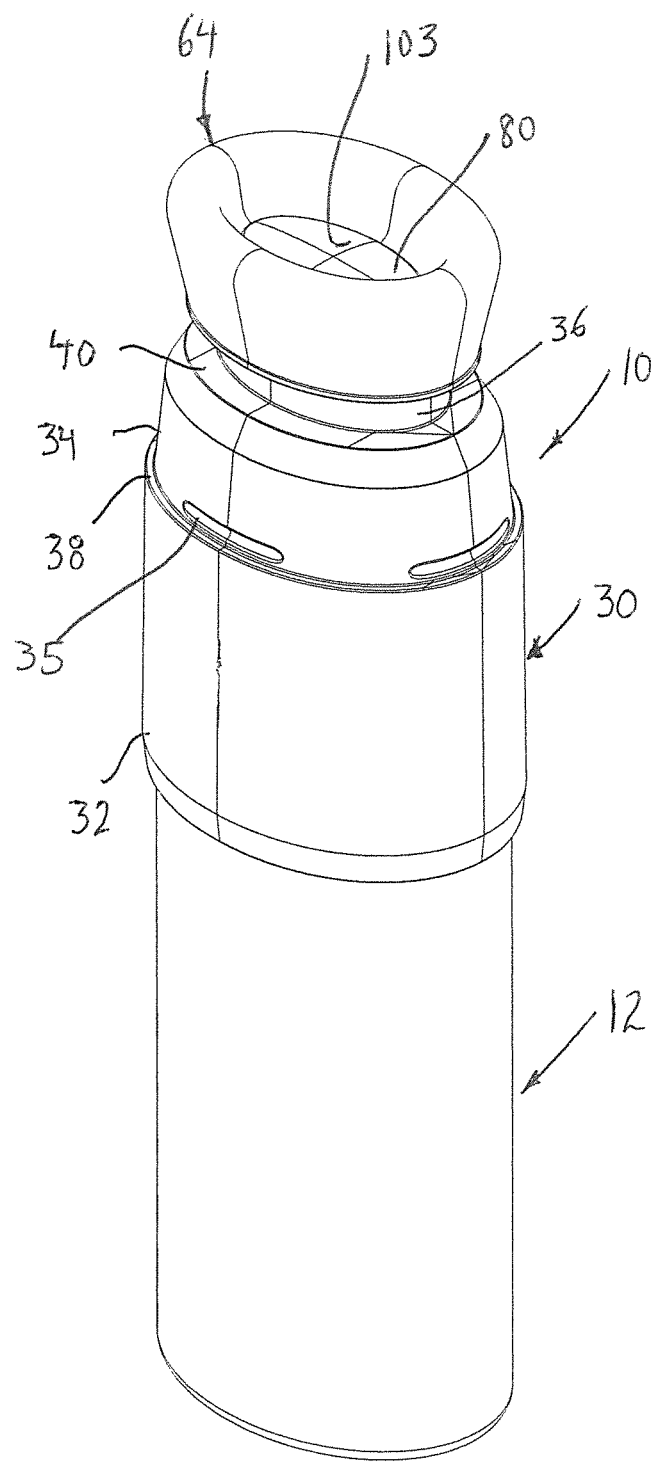
FIG. 2 is a perspective view of the applicator according to the present invention, mounted on a dispenser bottle, with the cap removed.

Referring to the drawings in detail, there is shown in FIG. 1 an embodiment of applicator 10 for applying a fluid to a surface according to the present invention.

Reference to a "surface" is used herein to include any solid or semi-solid material having one or more areas capable of being contacted with an applicator, such as woods, metals, minerals, ceramics, glasses, plastics, polymers, composite materials, and the like, as well as animal surfaces, such as skin and other organ surfaces. Reference to a "fluid" used herein is intended to include any flowable substance, such as liquids, solutions, foams, lotions, gels, creams, pastes, and the like. Embodiments of the applicator described herein have particular utility in the application of a medicated topical or transdermal fluid containing testosterone to the axilla of a human. In this way, contact of the medicated fluid with the user's hand can be avoided, thereby minimizing unintended interpersonal transfer of testosterone.

Figure 3:
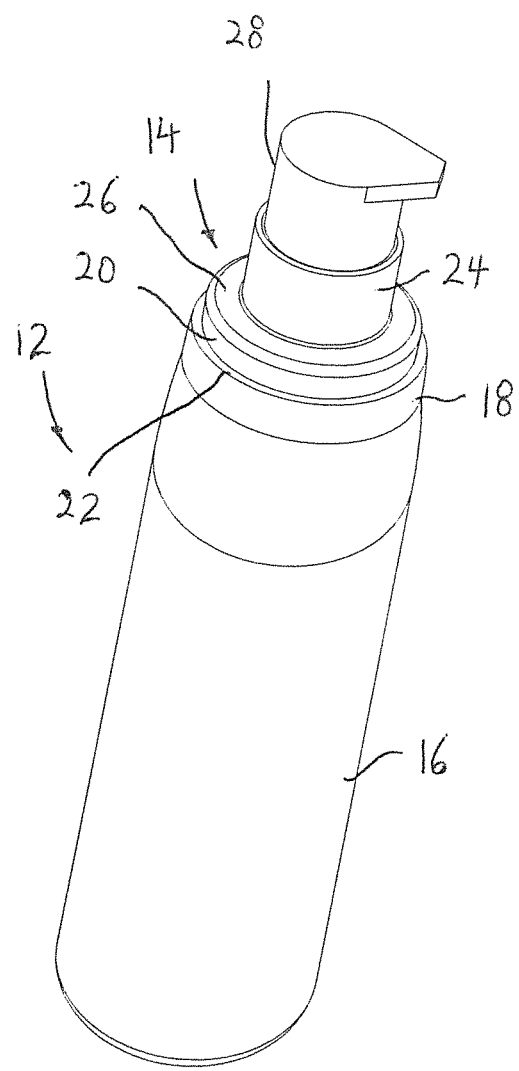
FIG. 3 is a perspective view of a dispenser bottle on which the applicator according to the present invention is adapted to be mounted.
Figures 4, 5:
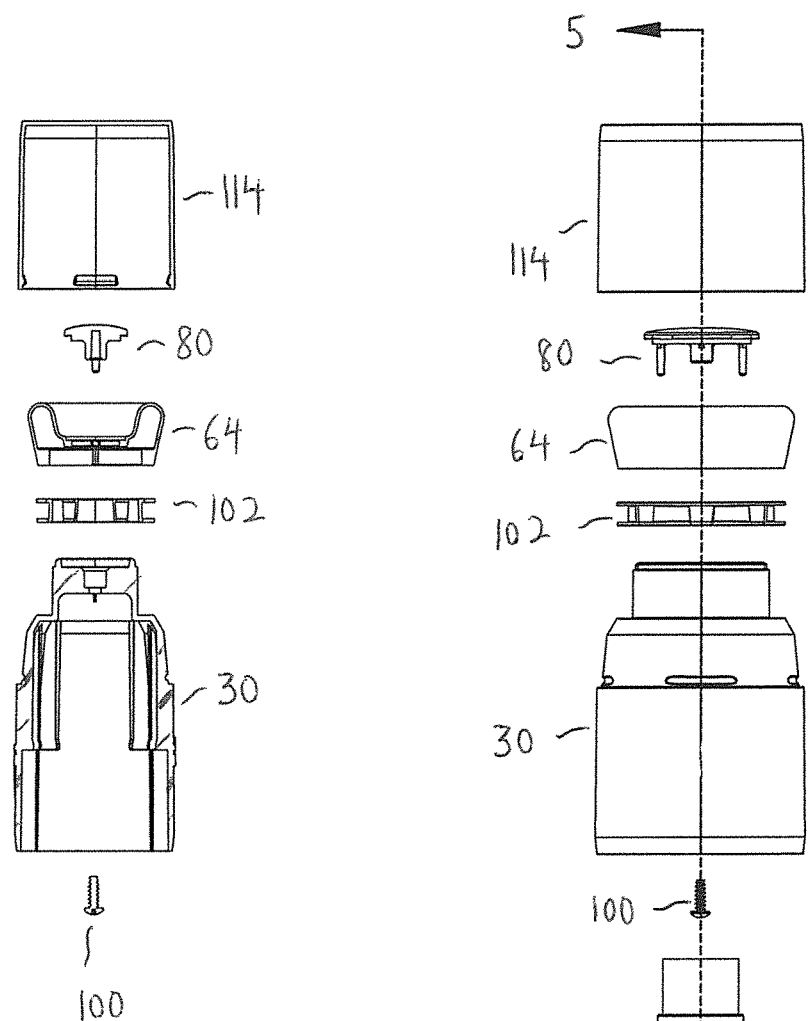
FIG. 4 is an exploded, front elevational view of the applicator and dispenser bottle.
FIG. 5 is a cross-sectional view of the applicator of FIG. 4, taken along line 5-5 thereof.
Figure 8:
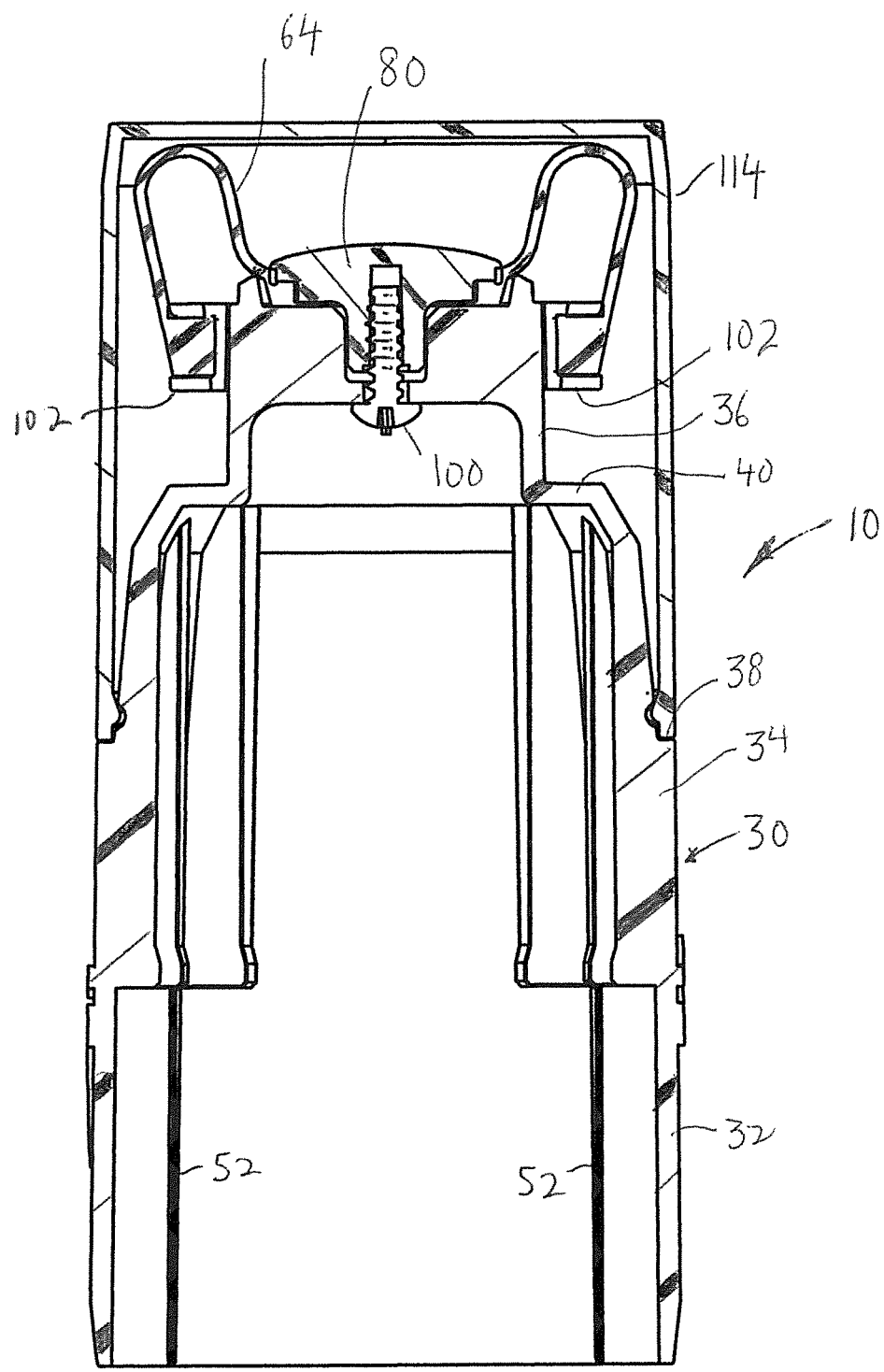
FIG. 8 is an enlarged cross-sectional view of the applicator of FIG. 5 in assembled form.
Figure 9:
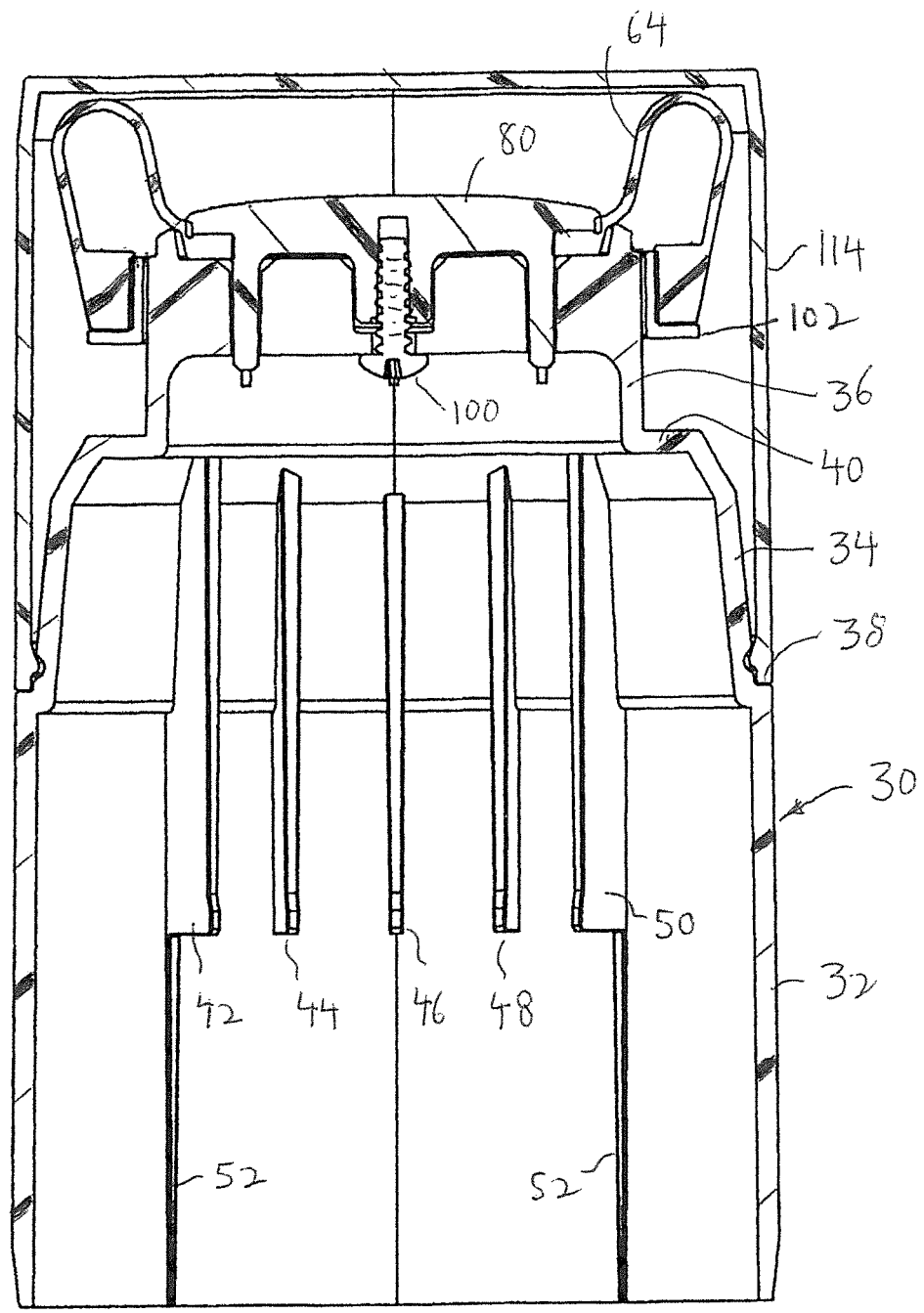
FIG. 9 is an enlarged cross-sectional view of the applicator of FIG. 7 in assembled form.
Figure 10:
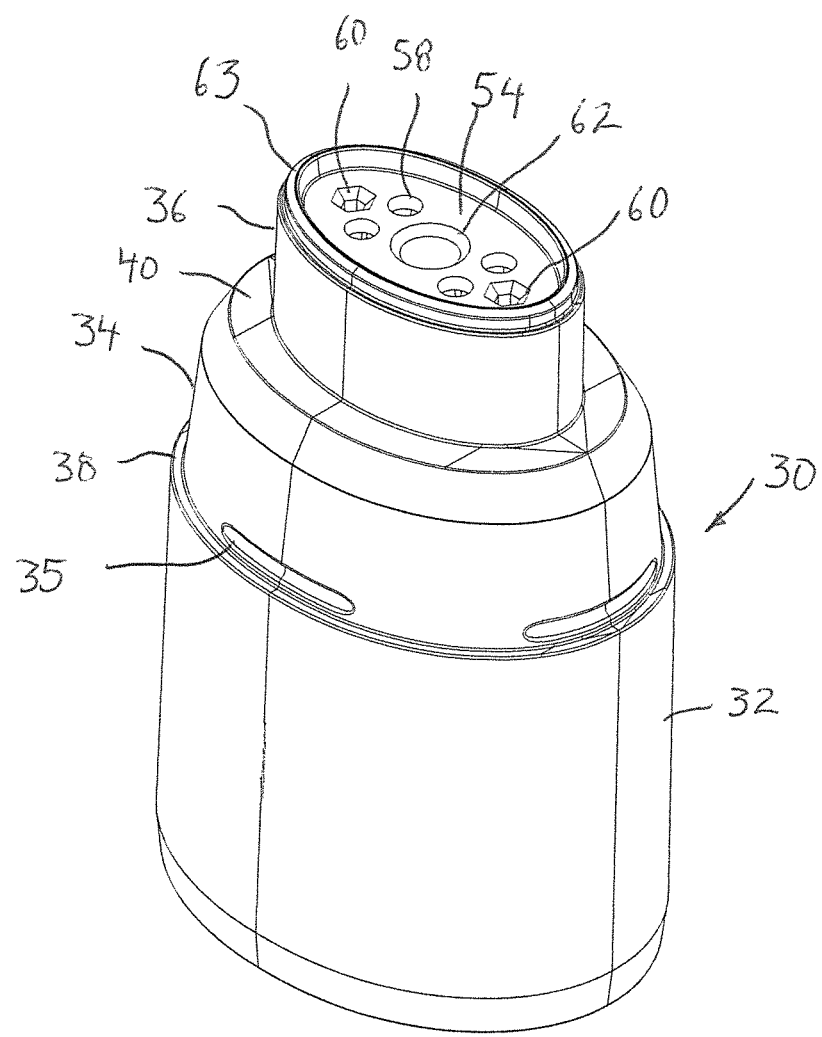
FIG. 10 is a top perspective view of the rigid support of the applicator.
Figure 11:
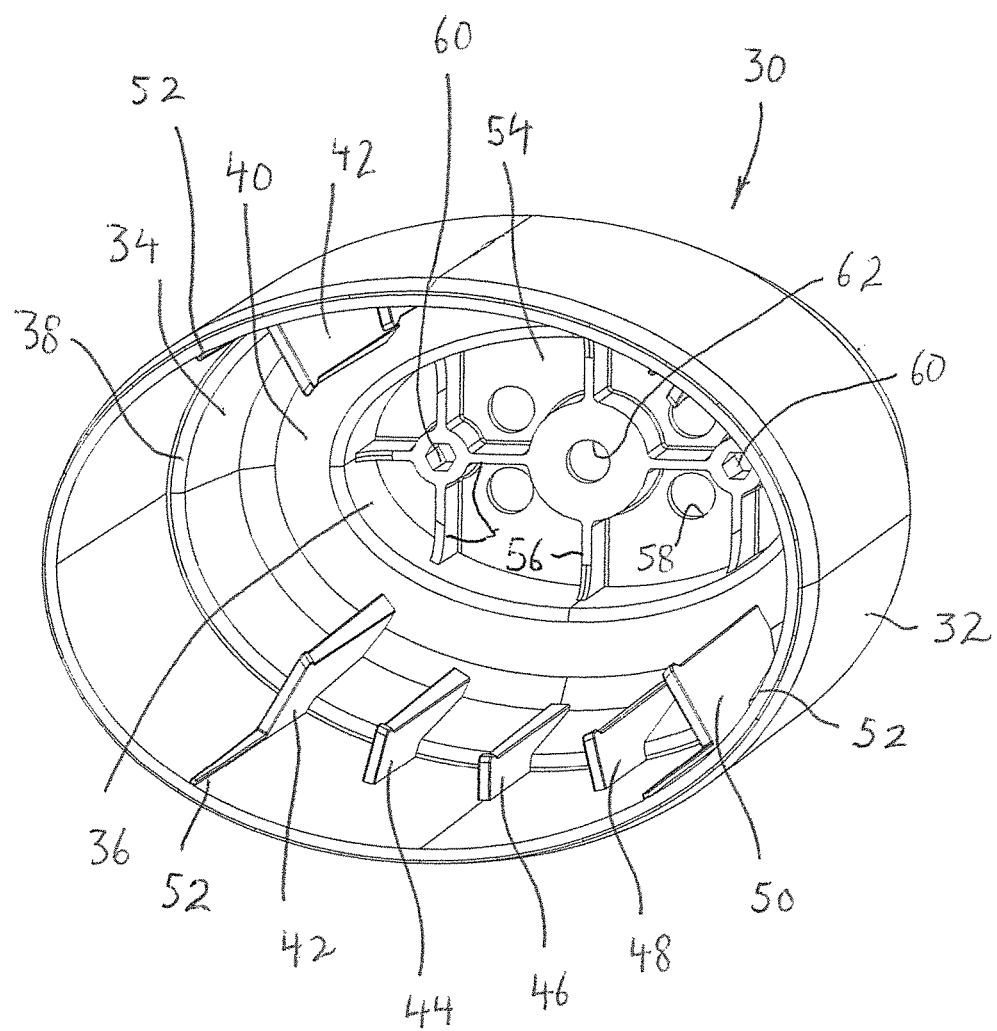
FIG. 11 is a bottom perspective view of the rigid support.
Figure 12:
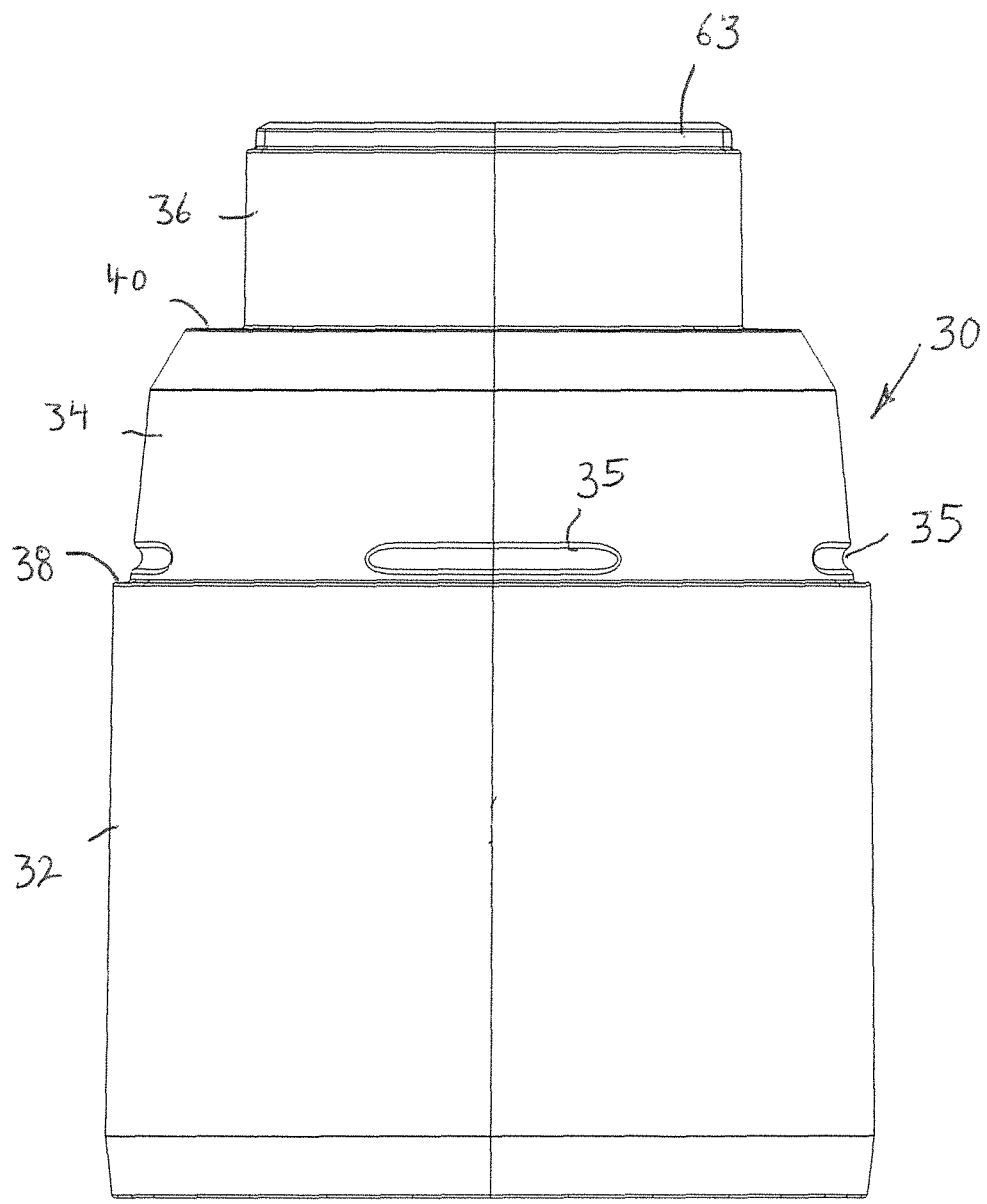
FIG. 12 is a front elevational view of the rigid support.
Figure 13:
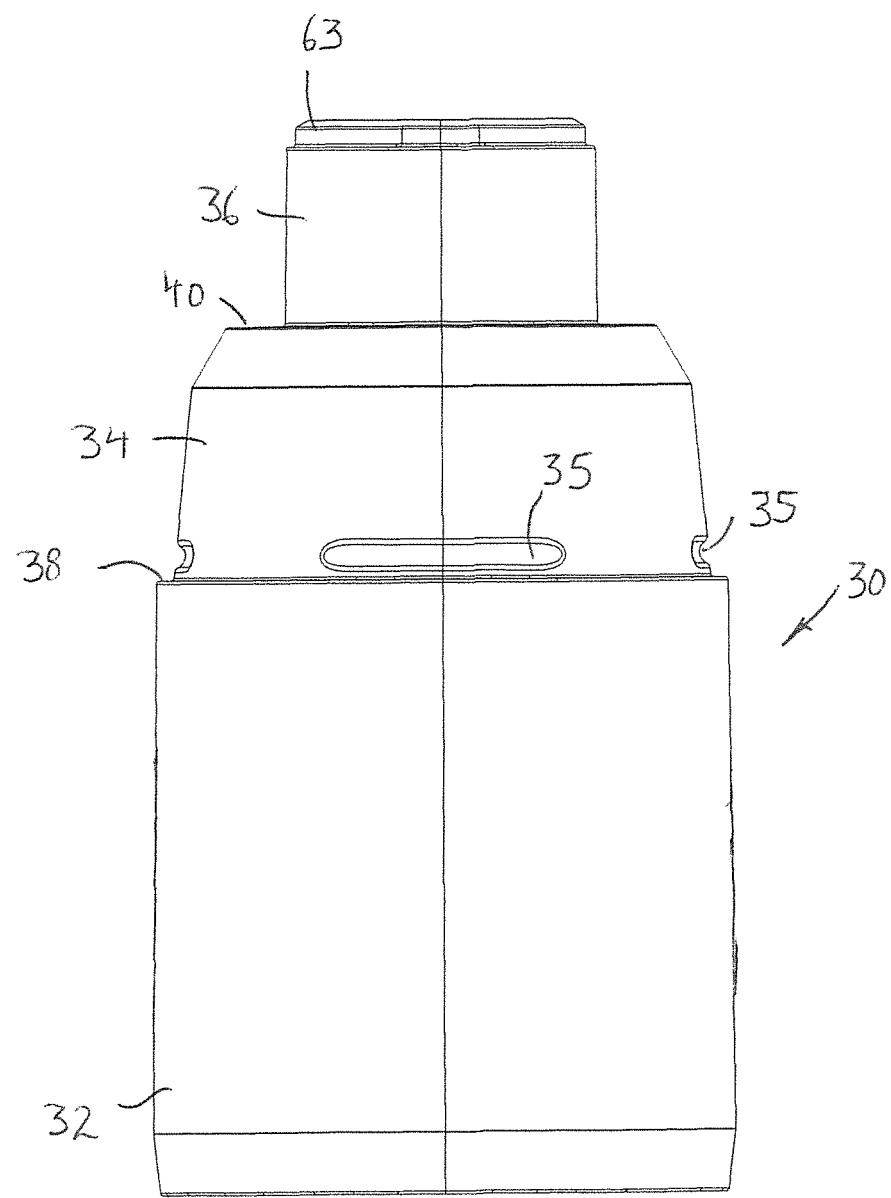
FIG. 13 is a side elevational view of the rigid support.
Figure 14:
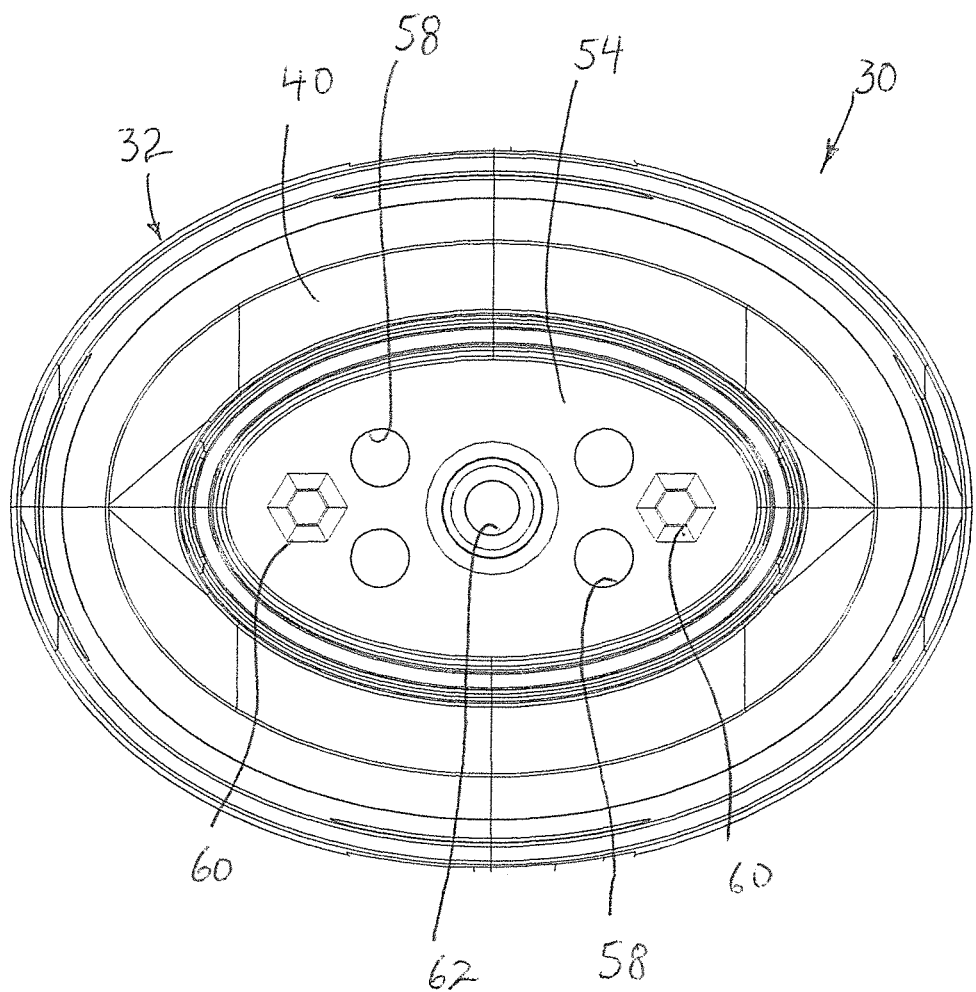
FIG. 14 is a top plan view of the rigid support.
Figure 15:
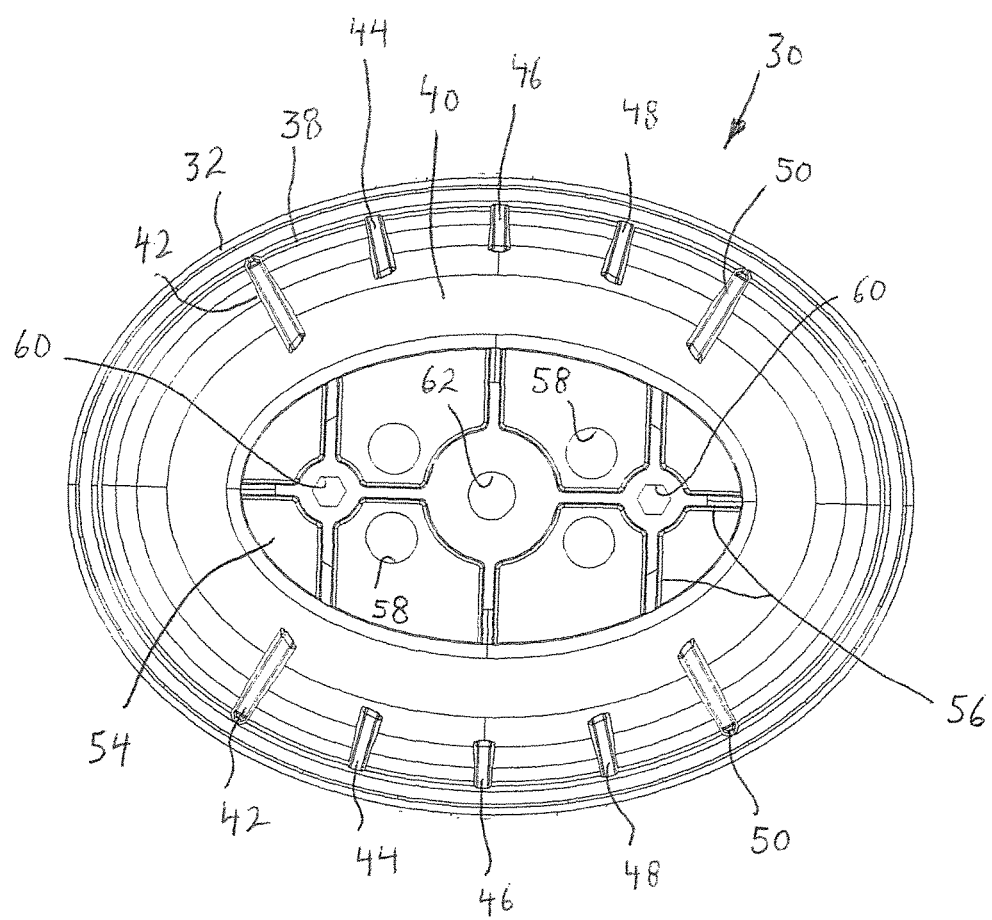
FIG. 15 is a bottom plan view of the rigid support.
Figure 16:
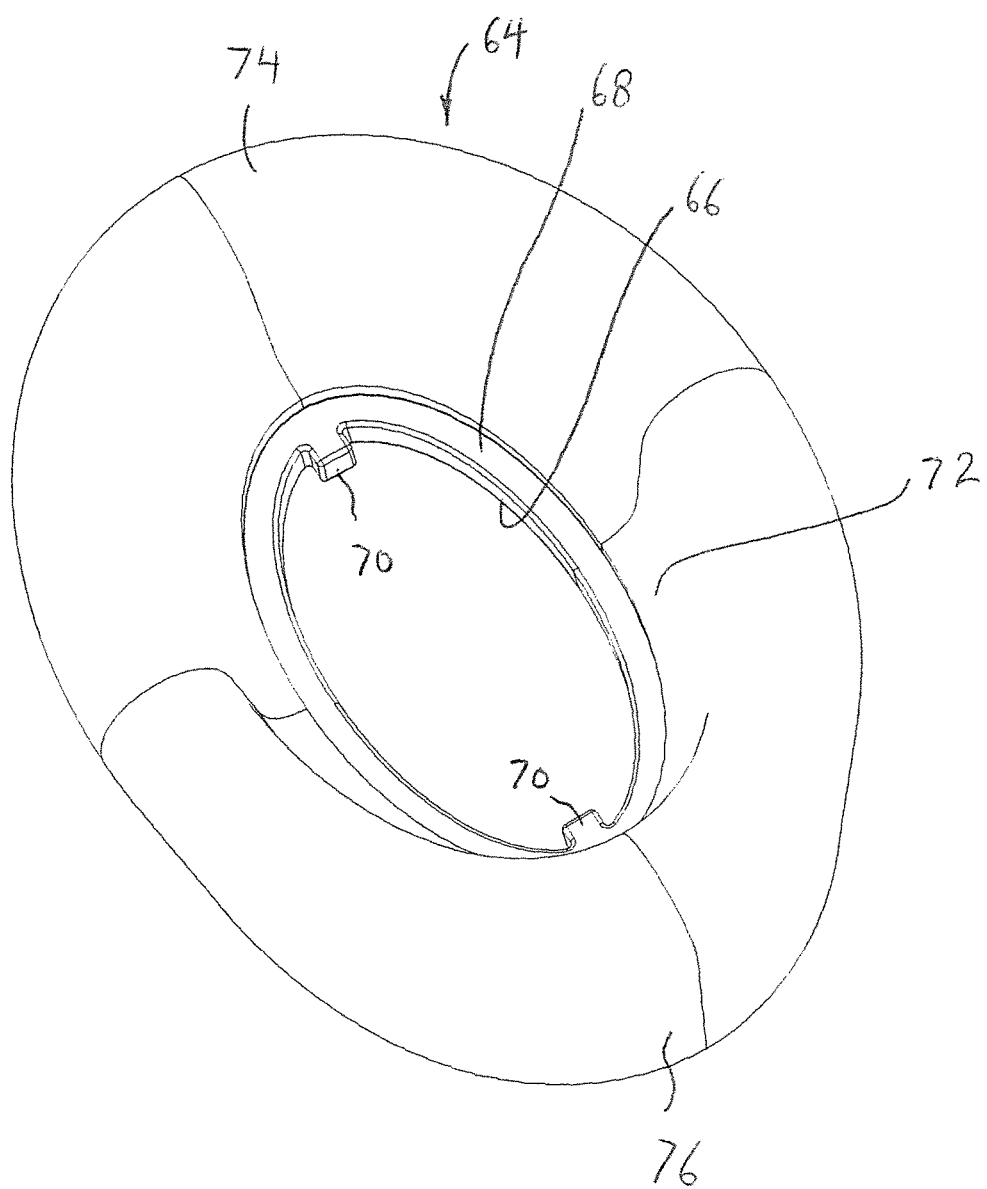
FIG. 16 is a top perspective view of the diaphragm of the applicator.
Figure 17:
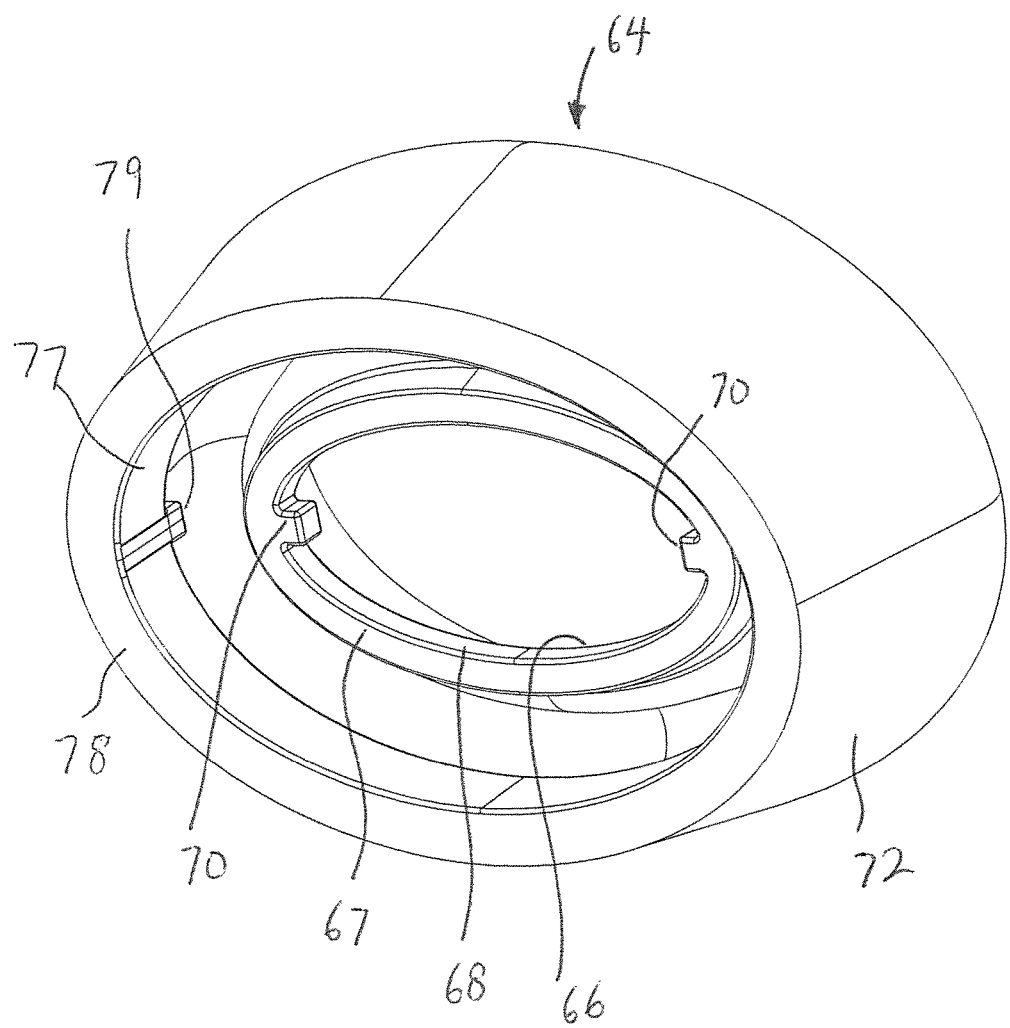
FIG. 17 is a bottom perspective view of the diaphragm.
Figure 18:
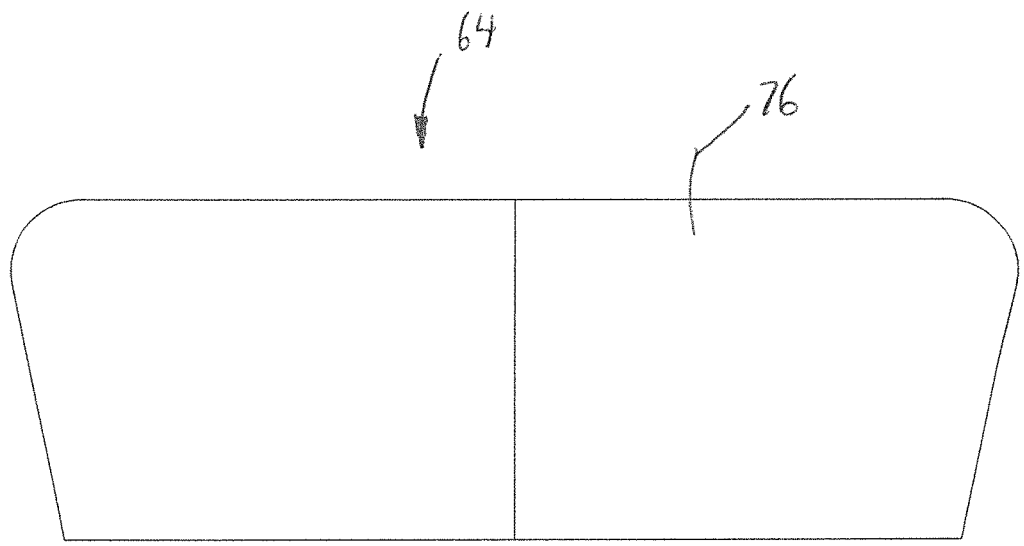
FIG. 18 is a front elevational view of the diaphragm.
Figure 19:
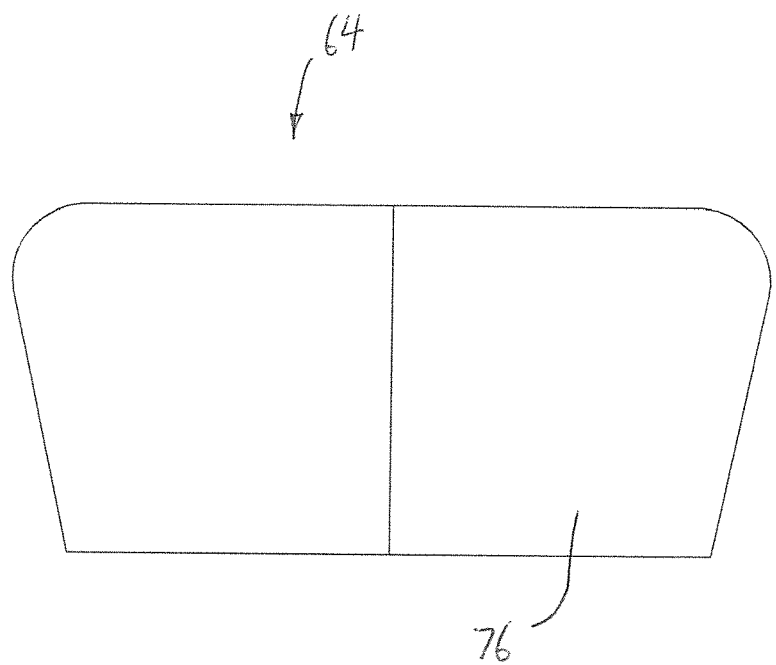
FIG. 19 is a side elevational view of the diaphragm.
Figure 20:
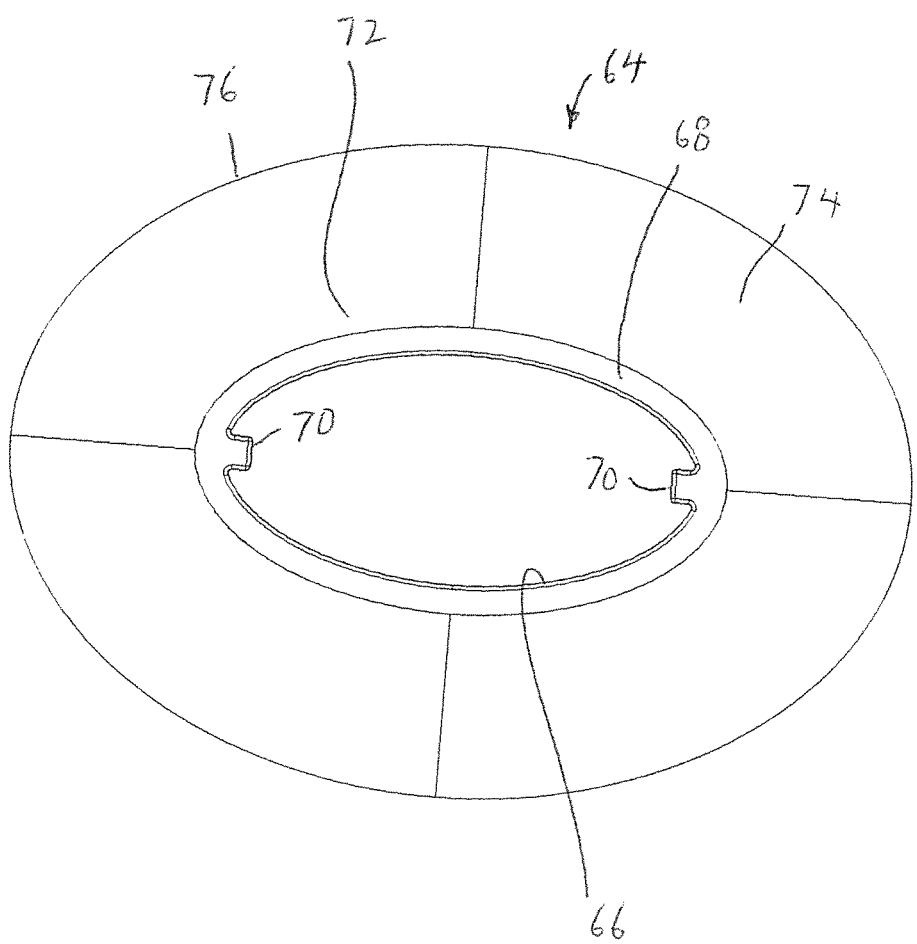
FIG. 20 is a top plan view of the diaphragm.
Figure 21:
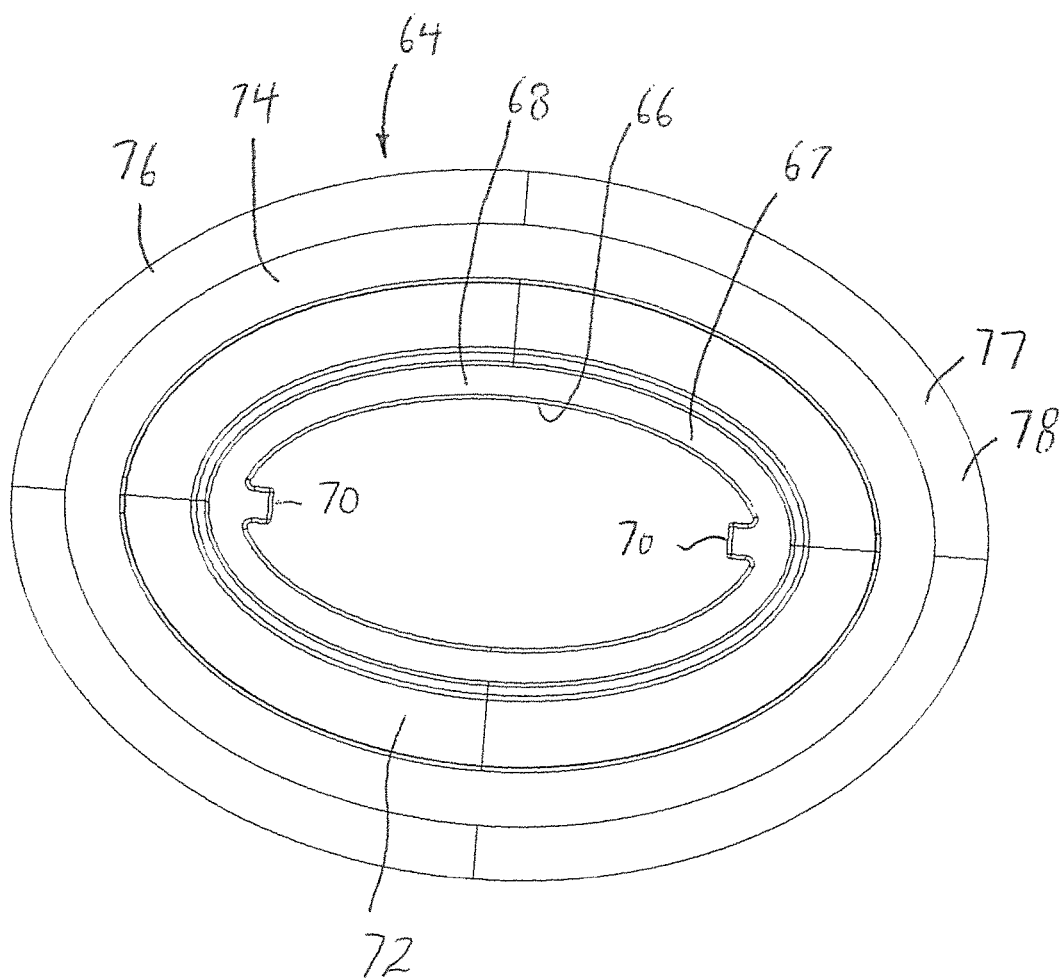
FIG. 21 is a bottom plan view of the diaphragm.
Figure 22:
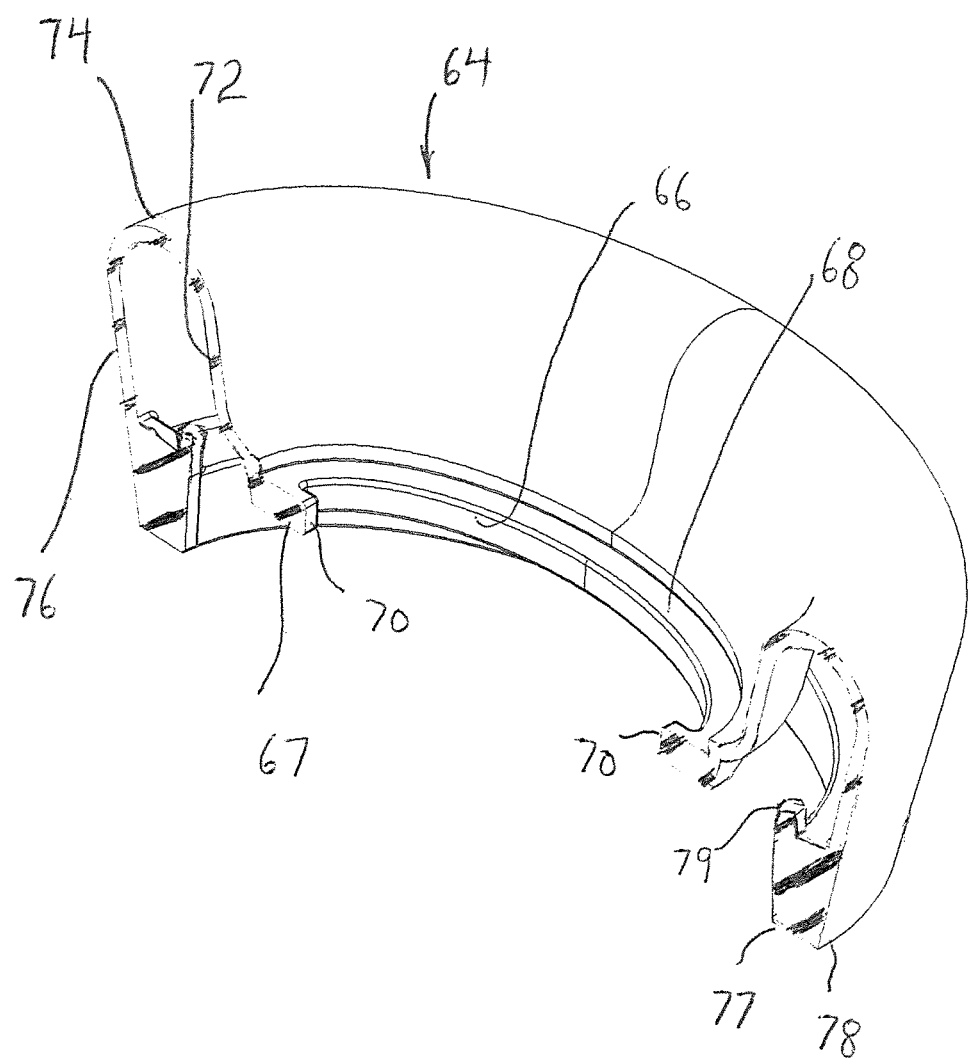
FIG. 22 is a longitudinal cross-sectional view of the diaphragm.
Figure 23:
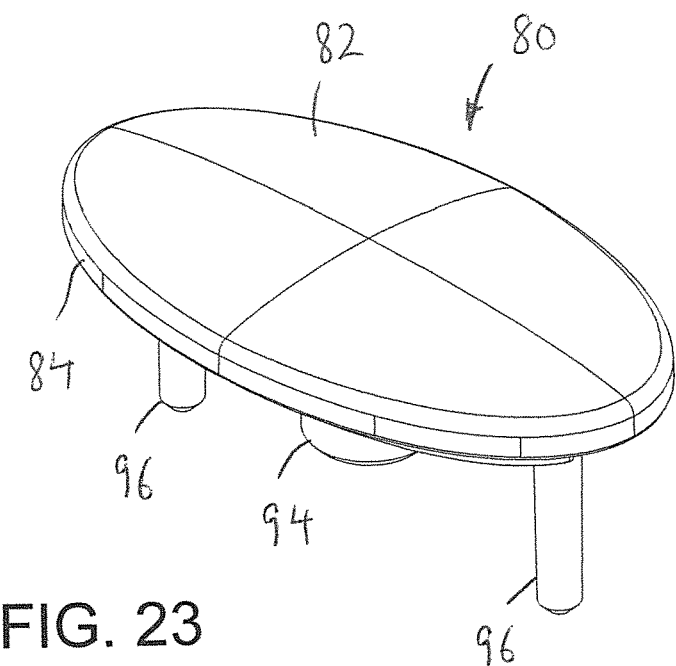
FIG. 23 is a top perspective view of the diaphragm holder of the applicator.
Figure 24:
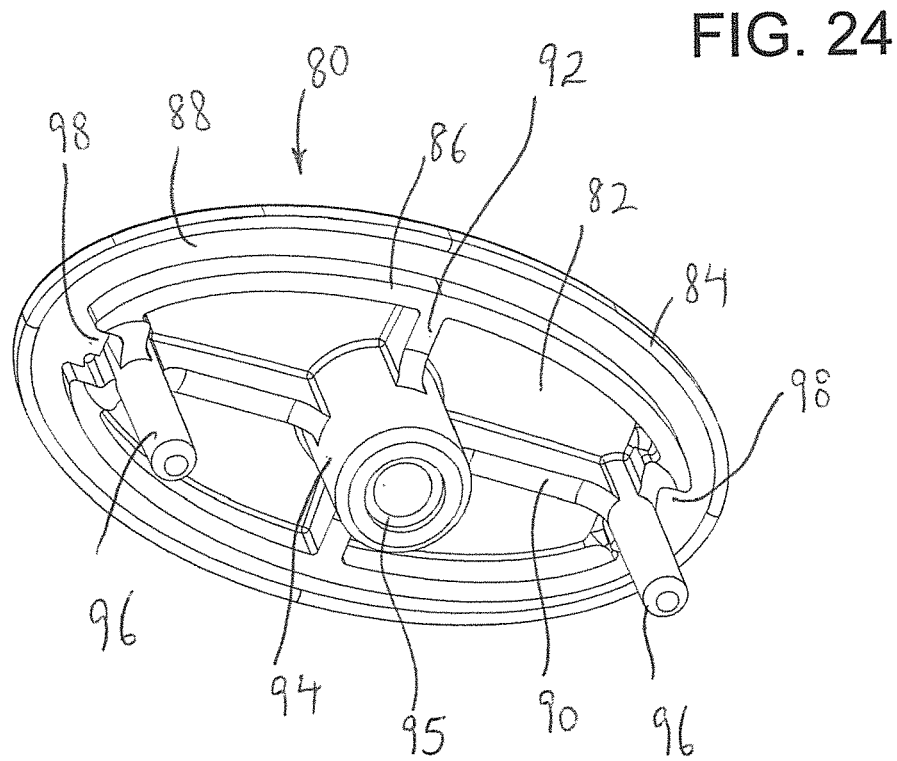
FIG. 24 is a bottom perspective view of the diaphragm holder.
Figure 25:
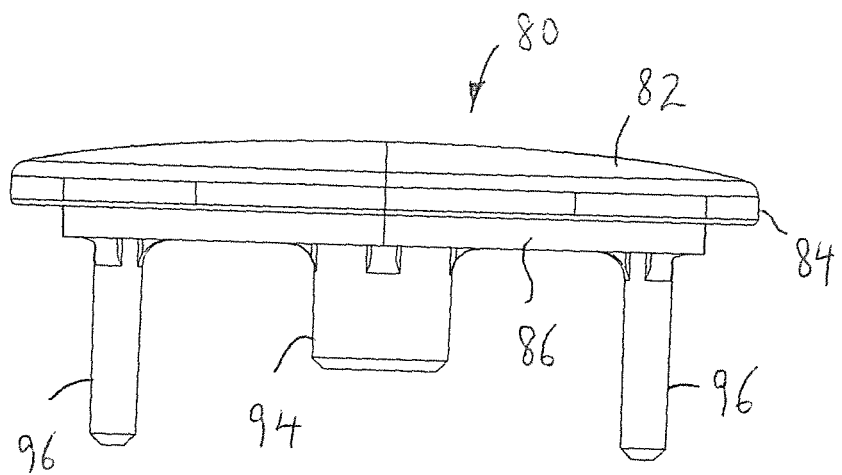
FIG. 25 is a front elevational view of the diaphragm holder.
Figure 26:
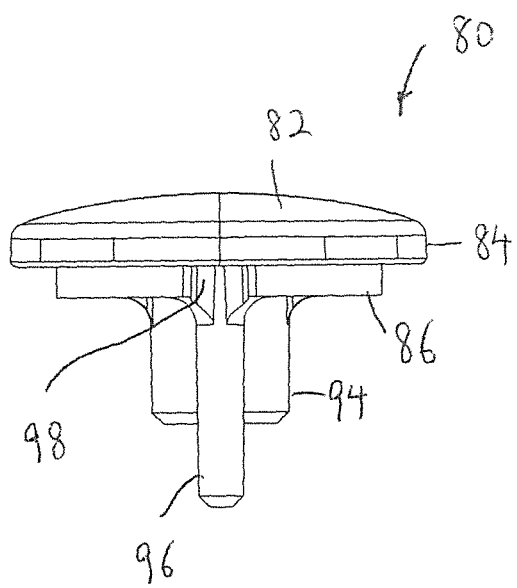
FIG. 26 is a side elevational view of the diaphragm holder.
Figure 27:
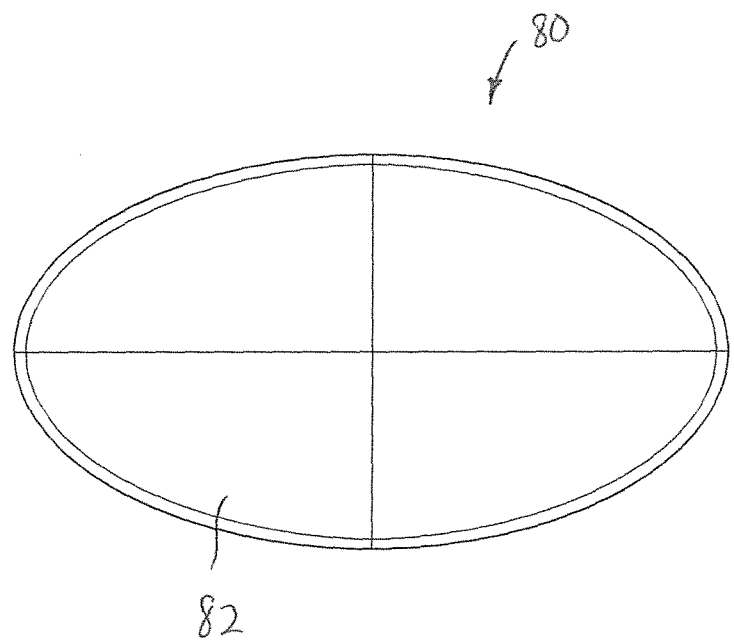
FIG. 27 is a top plan view of the diaphragm holder.
Figure 28:
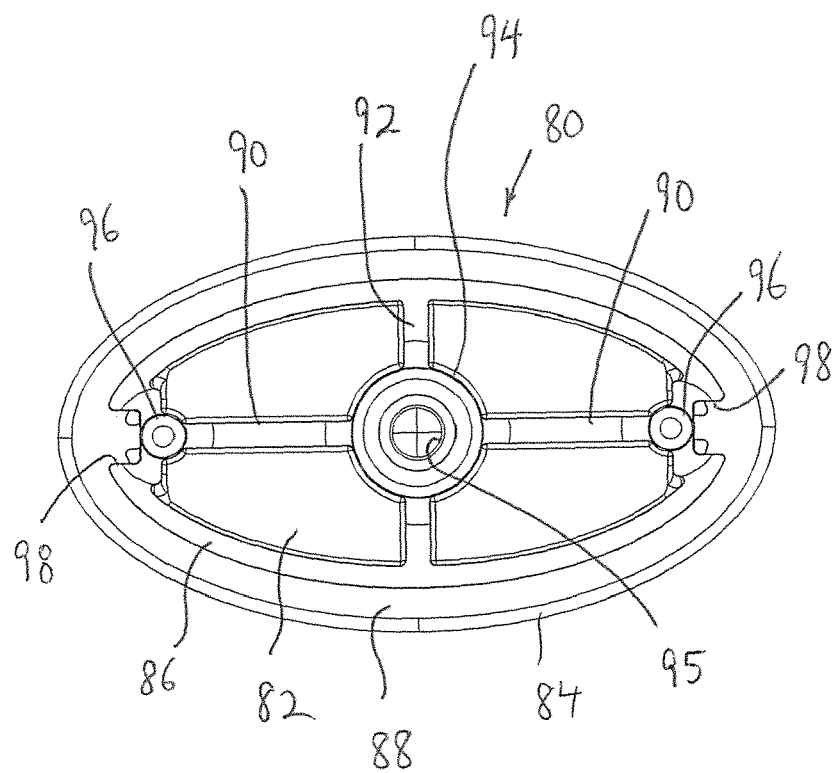
FIG. 28 is a bottom plan view of the diaphragm holder.
Figure 29:
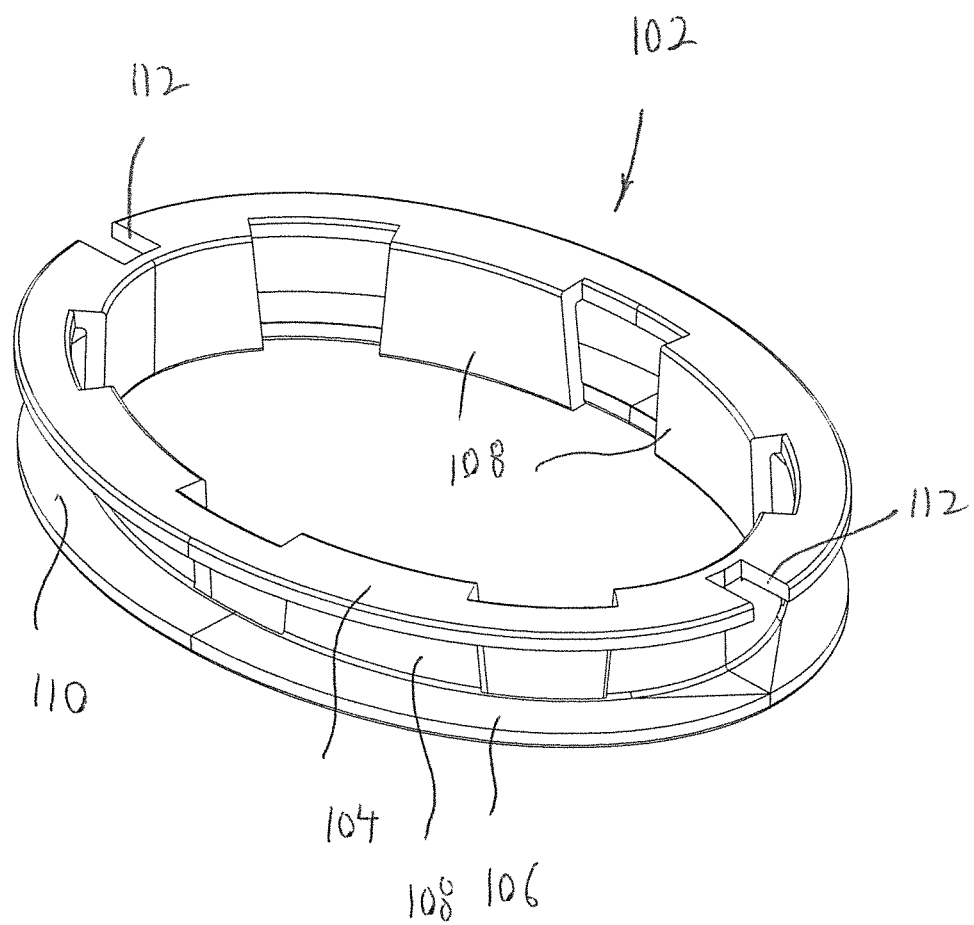
FIG. 29 is a top perspective view of the skirt of the applicator.
Figure 30:
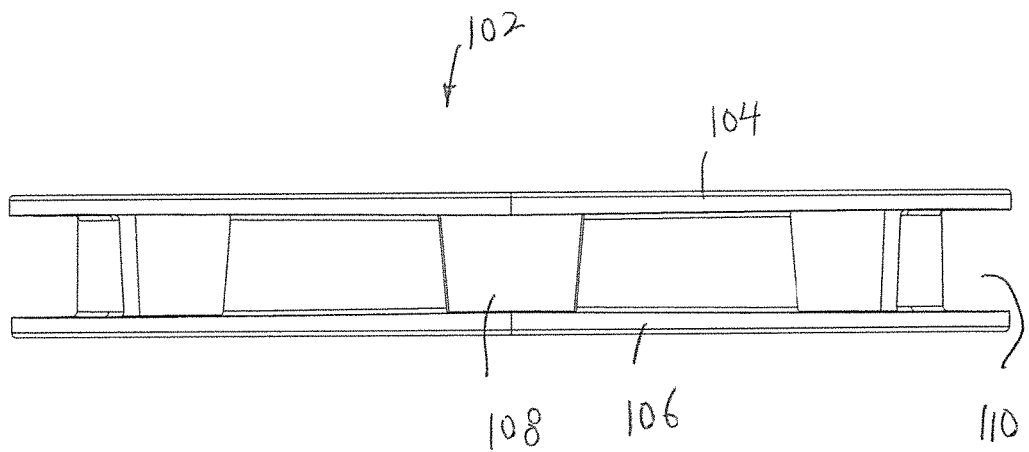
FIG. 30 is a front elevational view of the skirt.
Figure 31:
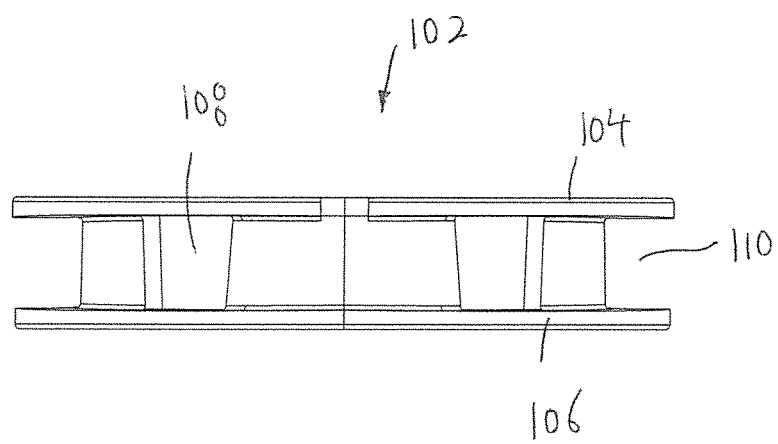
FIG. 31 is a side elevational view of the skirt.
Figure 32:
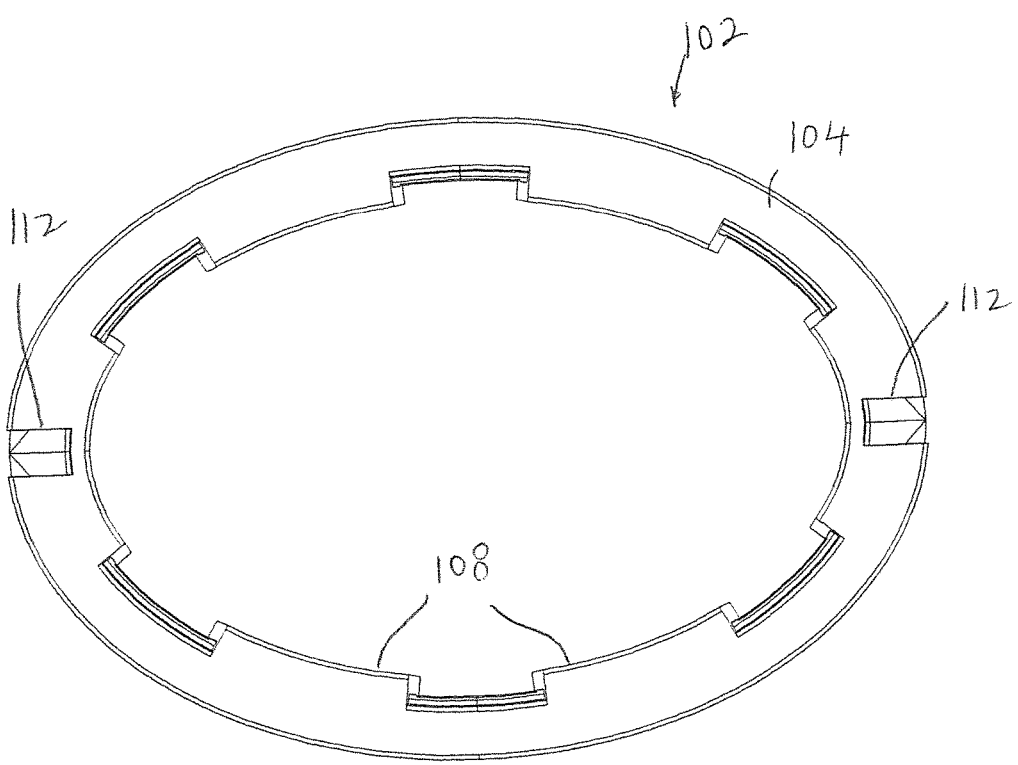
FIG. 32 is a top plan view of the skirt.
Figure 33:
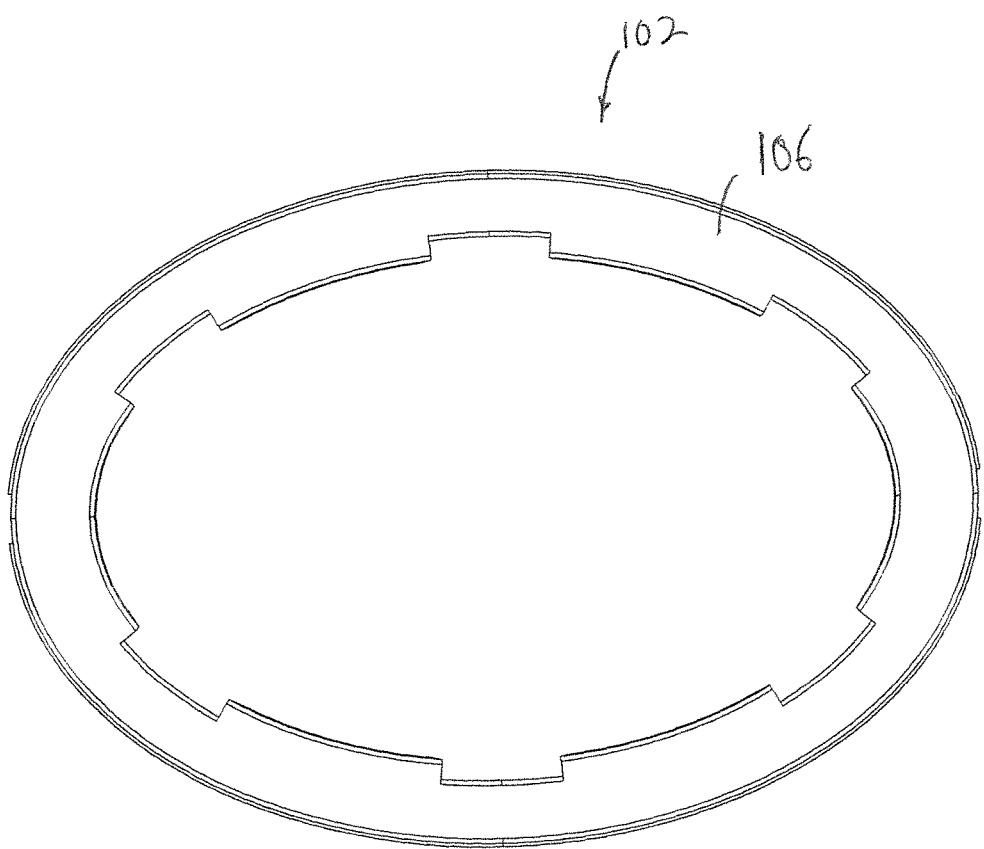
FIG. 33 is a bottom plan view of the skirt.

Applicator 10 is intended to seat upon the upper end of a bottle 12 containing the fluid, the bottle 12 having a pump dispenser 14 for dispensing the fluid to applicator 10 when applicator 10 is removed from bottle 12. As shown best in FIG. 3, bottle 12 has a main body 16 with a generally oval cross-sectional shape, and the upper open end of which is closed by pump dispenser 14. Pump dispenser 14 has a lower annular wall 18 of a first diameter that seats on the upper end of main body 16. The lower edge of an intermediate annular wall 20 of a second, smaller diameter is connected to the upper edge of lower annular wall 18 by an annular shoulder 22. The lower edge of an upper annular wall 24 of a third, still smaller diameter is connected to the upper edge of intermediate annular wall 20 by an annular shoulder 26. A pump 28 of the pump dispenser 14 is fit within upper annular wall 24 and operates in a well-known manner which is not described herein.

As shown in FIGS. 2 and 5-15, applicator 10 includes a thin walled, rigid support 30, preferably of a rigid plastic material, having a generally oval configuration, although the present invention is not limited to this configuration. Rigid support 30 functions as a handle or holder. Rigid support 30 is formed as a unitary, single piece structure, and is formed of three thin-walled sections 32, 34 and 36 connected to each other in succession. Lower section 32 has a generally oval shape similar to that of main body 16 and forms a holder by which a person can hold applicator 10 during use of applicator 10. Intermediate section 34 also has a generally oval shape but with slightly less dimensions than lower section 32, with the lower edge of intermediate section 34 connected to the upper edge of lower section 32 by an oval shoulder 38. Upper section 36 also has a generally oval shape but with smaller dimensions than intermediate section 34, with the lower edge of upper section 36 connected to the upper edge of intermediate section 34 by an oval shoulder 40.

Two sets of substantially parallel, spaced-apart ribs 42, 44, 46, 48 and 50 extend continuously along the inner surface of intermediate section 34 from the upper end thereof to a position about one-third of the way down the inner surface of lower section 32, with each set being in opposing relation to the other set and the ribs extending in the direction of the center axis of lower section 32. The inner edges of each rib 42, 44, 46, 48 and 50 extend around a circular area, and each rib faces inwardly along a radius of the circular area. Thus, because the inner surface of lower section 32 has an oval section, outer ribs 42 and 50 extend inwardly to a greater extent than middle ribs 44 and 48, and middle ribs 44 and 48 extend inwardly to a greater extent than the center rib 46. In this manner, when lower section 32 seats on main body 16 of bottle 12, the lower edges of ribs 42, 44, 46, 48 and 50 seat on annular shoulder 22, and the inner edges of ribs 42, 44, 46, 48 and 50 frictionally engage the outer surface of intermediate annular wall 20. In addition, further ribs 52 extend axially down from the lower ends of ribs 42 and to the lower edge of lower section 32, with ribs 52 having very small inward dimensions so as to effectively form small beads. When rigid support 30 is positioned on main body 16 such that ribs 42, 44, 46, 48 and 50 frictionally engage the outer surface of intermediate annular wall 20, ribs 52 function to provide some frictional engagement with the outer wall of main body 16 to prevent wobbling of rigid support 30 on main body 16.

The number of ribs can vary, as desired, for devices of different dimensions and materials of construction.

The outer surface of intermediate section 34 is provided with four equiangularly spaced elongated depressions 35 around a common peripheral line, immediately above shoulder 38, the purpose for which will be understood from the description hereafter.

The upper edge of upper section 36 is closed off by an upper oval shaped top wall 54, and reinforcing ribs 56 connect opposing inner surfaces of upper section 36 and are connected to the inner or lower surface of top wall 54. Vent openings 58 can be provided in top wall 54 between ribs 56. In addition, two guide openings 60 are provided in oval top wall 54 at opposite ends of the longer axis thereof, and a central securing opening 62 is provided along the same longer axis between guide openings 60. Vent openings 58 are provided to opposite sides of this longer axis. Lastly, an upper oval lip 63 extends upwardly, slightly inward from the outer periphery of top wall 54.

As shown best in FIGS. 2, 5-9 and 16-22, a thin-walled flexible membrane or diaphragm 64, in certain embodiments formed from a silicone rubber material (in particular medical grade silicone rubber where a medicated fluid is to be applied to skin), but not limited thereto, has a central opening 66 of an oval shape, with the inner periphery being thickened to form an oval shaped ring 68 of the same material, which also extends below central opening 66 to form an oval lip 67 and which has in-turned nubs 70 extending inwardly toward each other along the large axis of the oval shape.

From the outer periphery of oval shaped ring 68, membrane 64 continues upwardly along an inner wall section 72, is folded over at its upper end to form an upper folded end 74 and then continues downwardly to form an outer wall section 76. Upper folded end 74 in this embodiment forms a continuous oval shape. However, unlike the lower end of the outer wall section of the implement of U.S. Pat. No. 8,177,449 to Bayly et al., which is fixed to the implement, the lower end 78 of outer wall section 76 according to the present invention is not fixed to support 30, and in fact, is free to move axially relative to upper section 36 during application of a fluid to the surface. As a result, when the user applies membrane 64 to the surface, and pressure is applied to the upper folded end 74, lower end 78 moves distally down upper section 36 towards middle section 34, resulting in little to no lateral deformation of upper folded end 74 against the surface. Rather, upper folded end 74 deforms relatively uniformly around its perimeter along an axis that is transverse to central opening 66, resulting in more of a rolling action, which allows for a tighter seal with the surface. In certain embodiments, a vacuum seal is created. As a result, relatively less leakage of fluid may occur when membrane 64 is moved laterally across the surface. When applied to a skin surface, pulling of hair may be reduced during lateral movement of membrane 64.

As will be appreciated from the discussion hereafter, lower end 78 is thickened with the same material, to form an oval shaped lip 77 extending inwardly from lower end 78, with lip 77 having a generally square or rectangular cross-section, and with opposite nubs 79 extending upwardly in an axial direction at an upper surface of lip 77 at the inner periphery thereof, along the long axis of the oval shape of lip 77.

Oval shaped ring 68 is fixed to the upper surface of oval shaped top wall 54 by a membrane holder 80, which is best shown in FIGS. 2, 5-9 and 23-28. Membrane or diaphragm holder 80 includes a generally oval plate 82 having a slightly convex upper surface, a downturned lip 84 at the outer periphery thereof, and an oval downturned wall 86 of greater height than lip 84 and spaced inwardly from downturned lip 84 to form an oval recess 88 therebetween. A long rib 90 extends between opposite sides of oval downturned wall 86 along the long axis thereof and a short rib 92 extends between opposite sides of oval downturned wall 86 along the short axis thereof, with both ribs also connected to the lower surface of plate 82. A central boss 94 extends downwardly from the lower surface of plate 82 at the intersection of ribs 90 and 92 and has an internal opening 95, preferably threaded. Two guide pins 96 extend down from opposite ends of long rib 90. In addition, oval downturned wall 86 includes cut-outs 98 at positions corresponding to the ends of long rib 90, to the outside of guide pins 96.

With this structure, after membrane 64 is positioned on rigid support 30 by positioning oval lip 67 on top wall 54 and within the confines of upper oval lip 63 thereof, membrane holder 80 is positioned on top of ring 68 such that downturned lip 84 at the outer periphery thereof sits on ring 68, and downturned wall 86 fits within the confines of ring 68. At the same time, nubs 70 of membrane fit within cut-outs 98. In this regard, nubs 70 and cut-outs 98 form first and second alignment elements, respectively.

At the same time, guide pins 96 fit through guide openings 60, and central boss 94 fits through central securing opening 62. Thereafter, a securement member 100 is threadedly screwed from below into internal opening 95 of central boss 94 to fixedly secure ring 68 to top wall 54 in a fluid sealing manner.

A reservoir 103 for holding a fluid is thereby defined by the upper surface of plate 82 of membrane holder (which now covers and closes central opening 66 of membrane 64) and the inner wall section 72 of membrane 64 extending upwardly therefrom. Where a medicated fluid is to be applied to skin, plate 82 is preferably made of a material that is compatible with the medicated fluid (e.g., does not leach) and is safe for contact with skin.

At this time, outer wall section 76 of membrane is positioned in surrounding relation to upper section 36 with the lower end 78 thereof being free and movable in the axial direction of upper section 36.

In order to better provide for controlled free sliding movement of lower end 78 of outer wall section 76, in a preferred embodiment best shown in FIGS. 29-33, lower end 78 is fixed over an oval skirt 102 which has larger dimensions than the outer dimensions of upper section 36 so that it too can move axially relative to upper section 36.

Skirt 102 is formed by an upper oval plate 104 and a lower oval plate 106 connected together in parallel, spaced apart relation by a plurality of equiangularly spaced connecting walls 108 connected at inner edges of plates 104 and 106. Thus, an oval recess 110 is defined by plates 104 and 106, and connecting walls 108. In addition, upper wall includes two small openings 112 at the outer edge thereof in opposing relation to each other along the long axis of the oval shape of skirt 102. Accordingly, oval shaped lip 77 of membrane 64 fits within oval recess 110 and is retained therein. At the same time, nubs 79 of membrane 64 fit within small openings 112.

Figure 34:
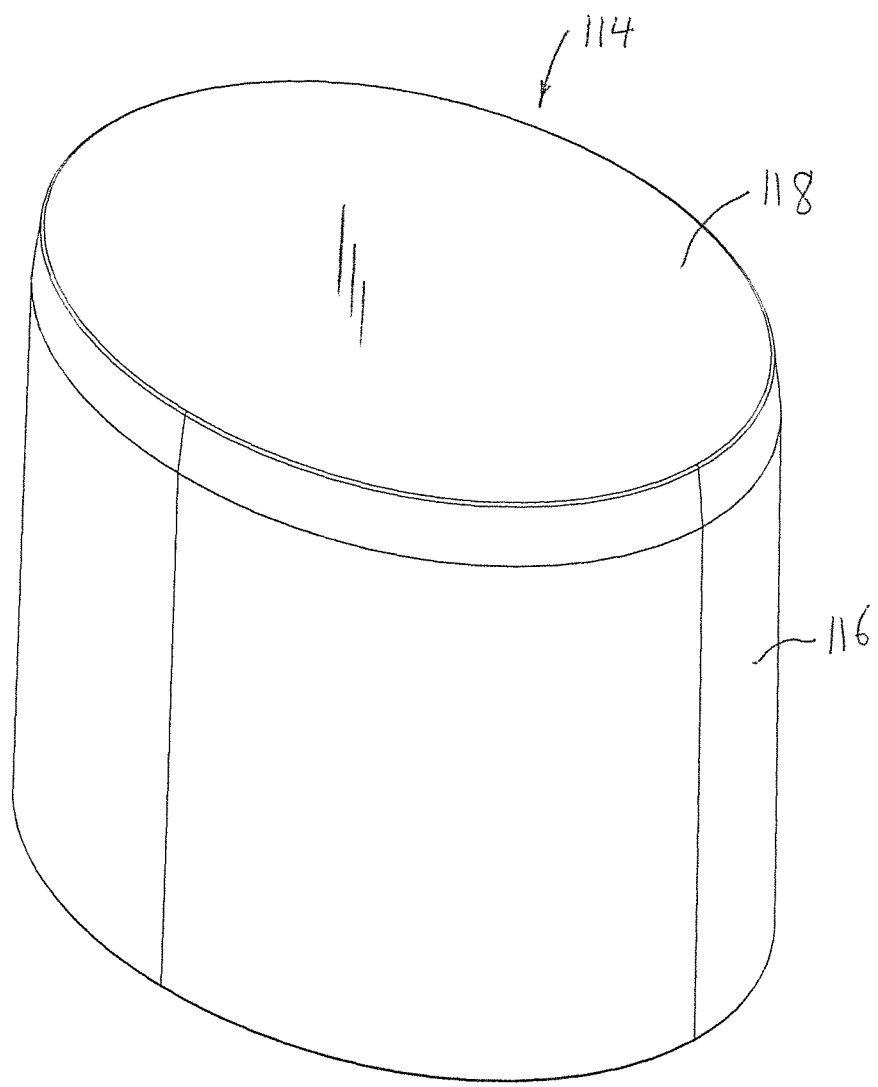
FIG. 34 is a top plan view of the cap.
Figure 35:
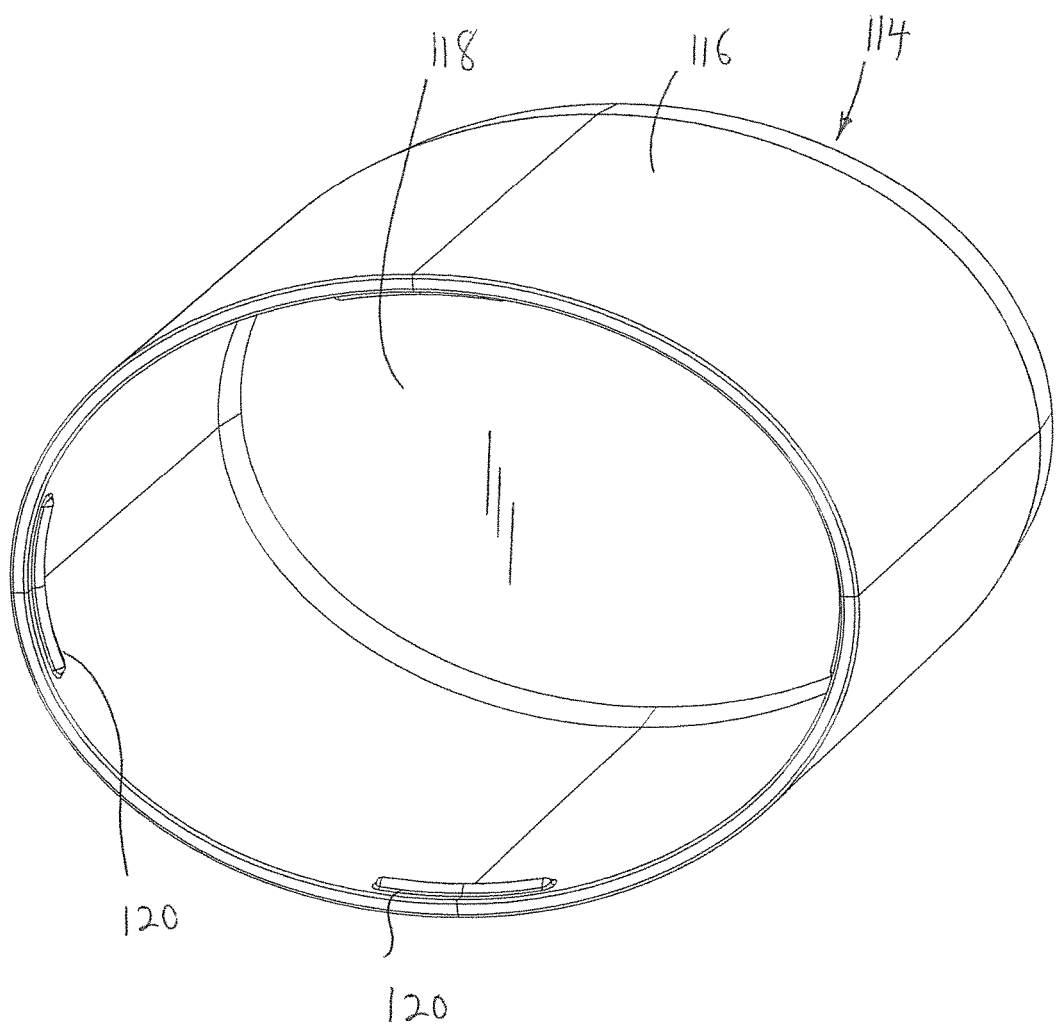
FIG. 35 is a bottom plan view of the cap.
Figures 36, 37:
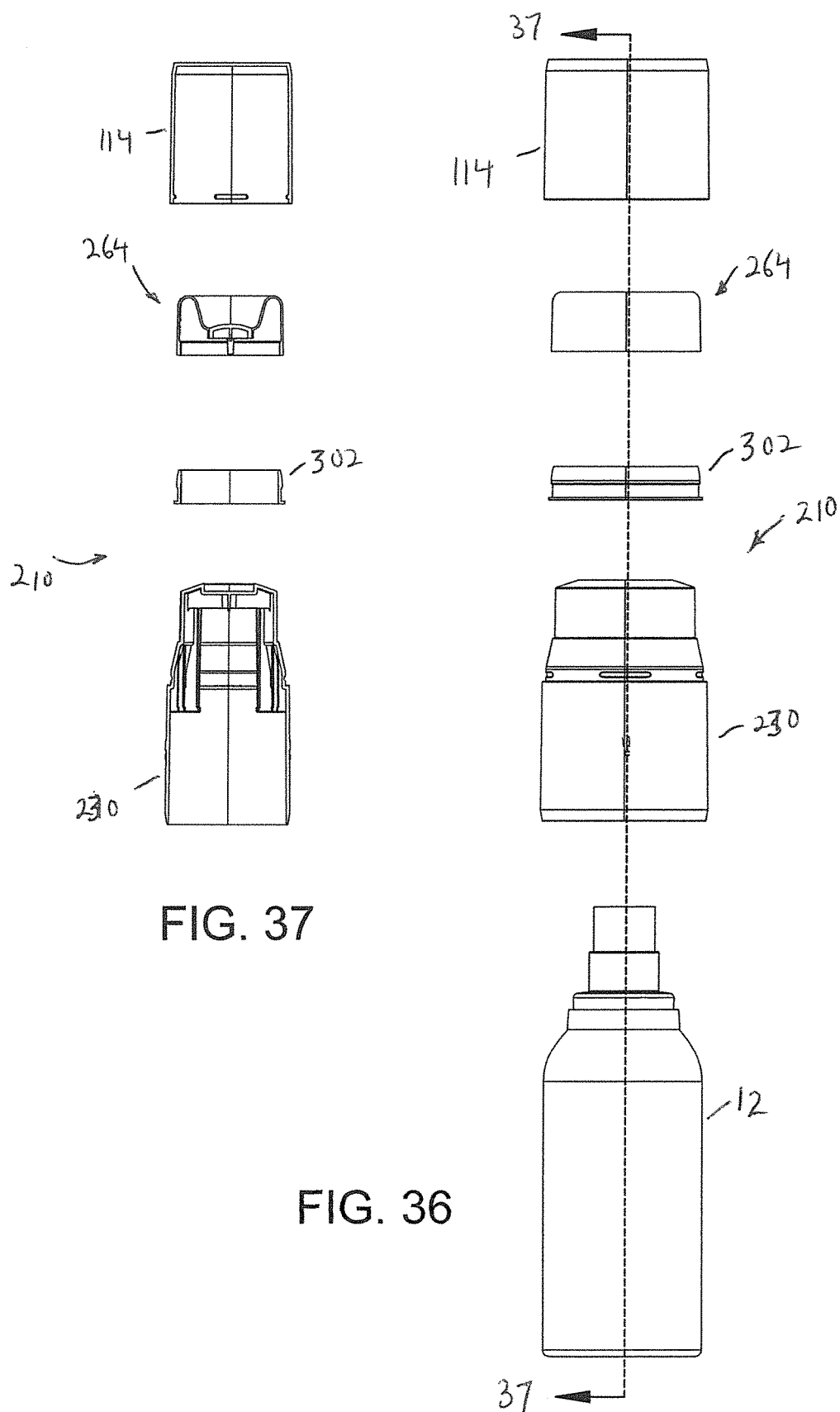
FIG. 36 is an exploded, front elevational view of the modified applicator and dispenser bottle.
FIG. 37 is a cross-sectional view of the applicator of FIG. 36, taken along line 37-37 thereof.
Figure 39:
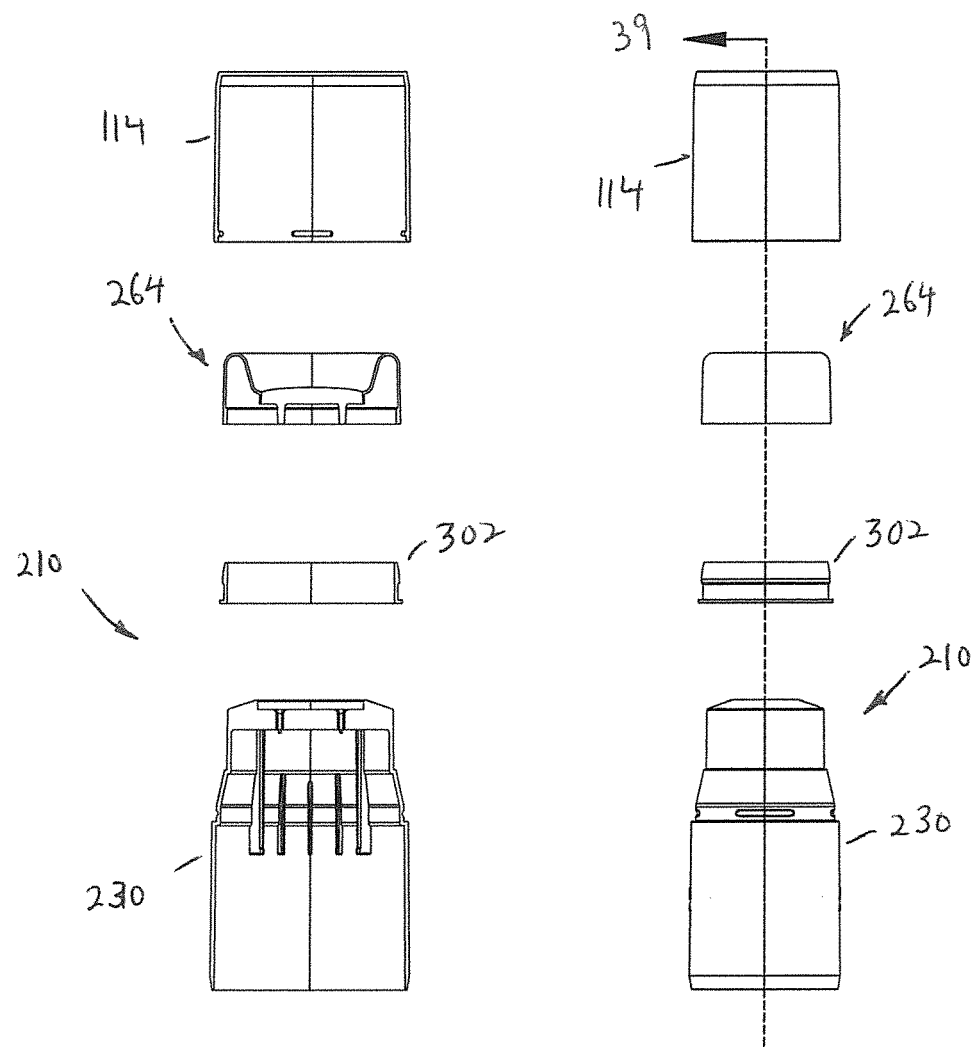
FIG. 39 is a cross-sectional view of the applicator of FIG. 38, taken along line 39-39 thereof.
Figure 38:
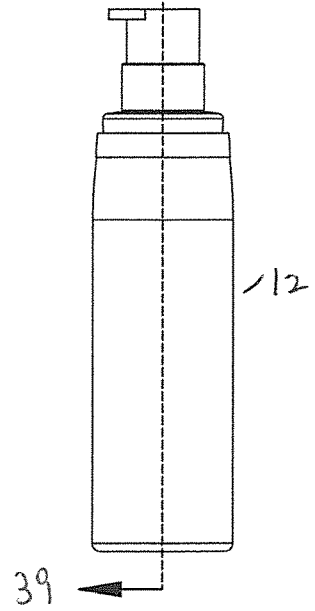
FIG. 38 is an exploded, side elevational view of the modified applicator and dispenser bottle.
Figure 42:
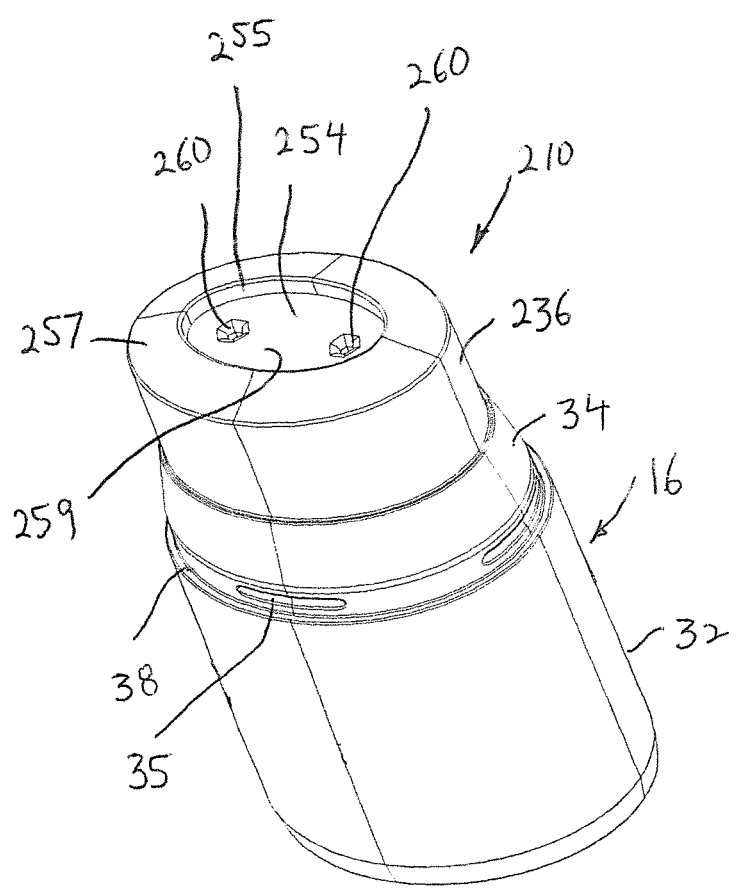
FIG. 42 is a top perspective view of the rigid support of the applicator of FIG. 36.
Figure 43:
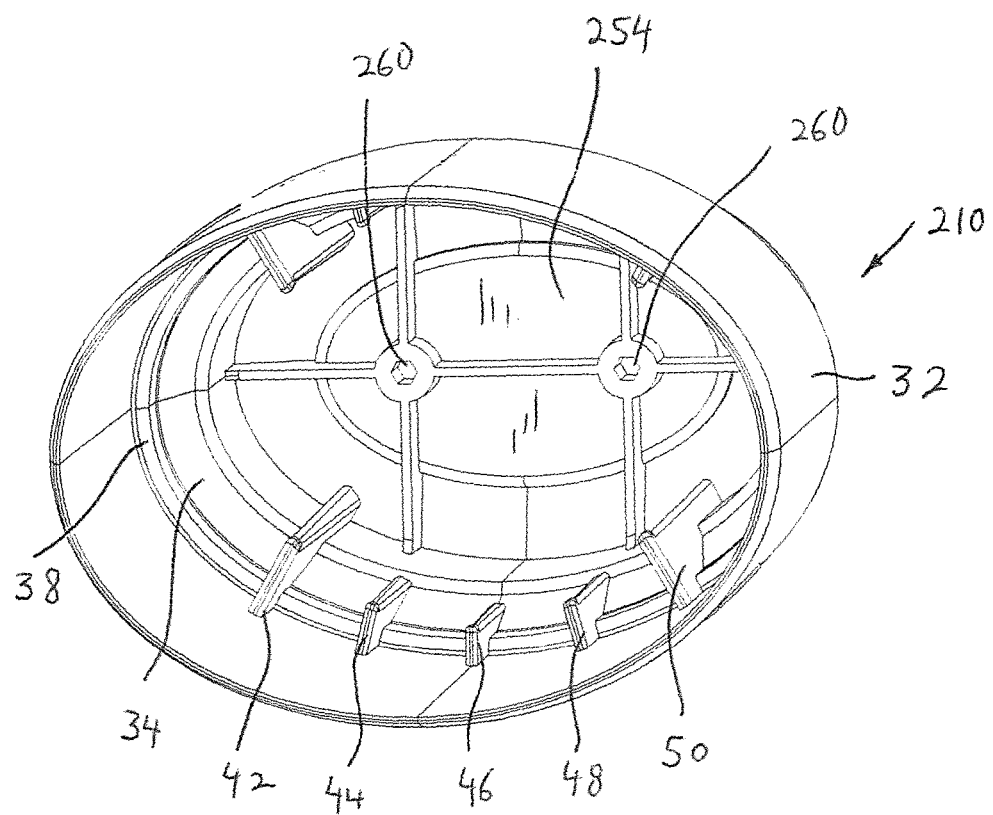
FIG. 43 is a bottom perspective view of the rigid support of FIG. 42.
Figure 44:
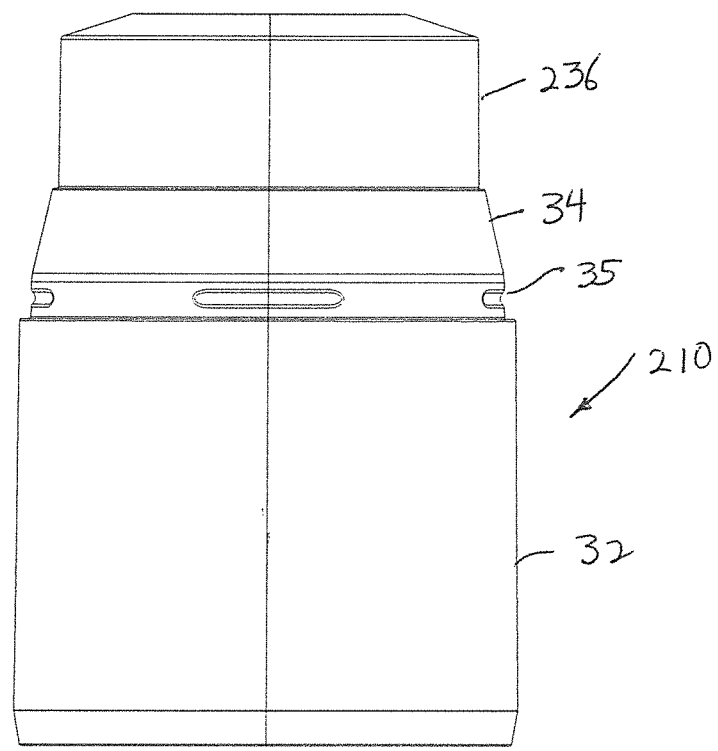
FIG. 44 is a front elevational view of the rigid support of FIG. 42.
Figure 45:
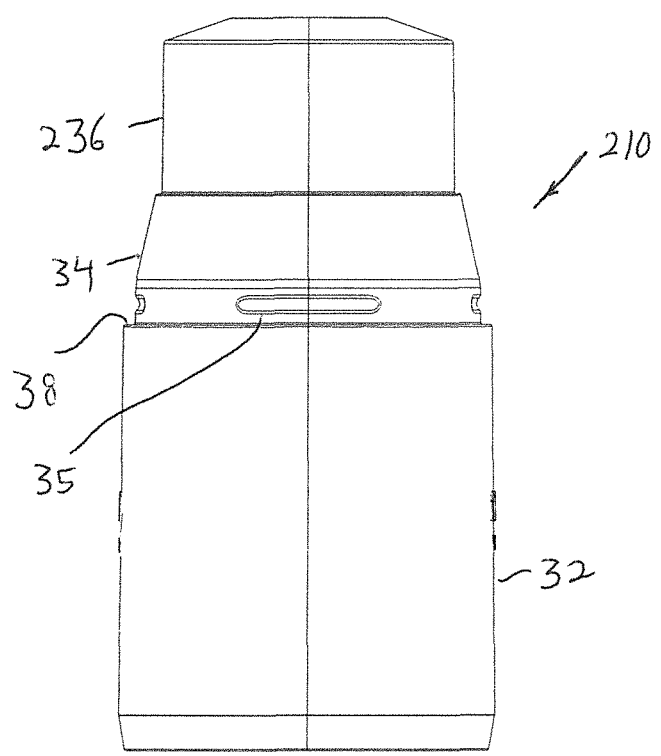
FIG. 45 is a side elevational view of the rigid support of FIG. 42.
Figure 46:
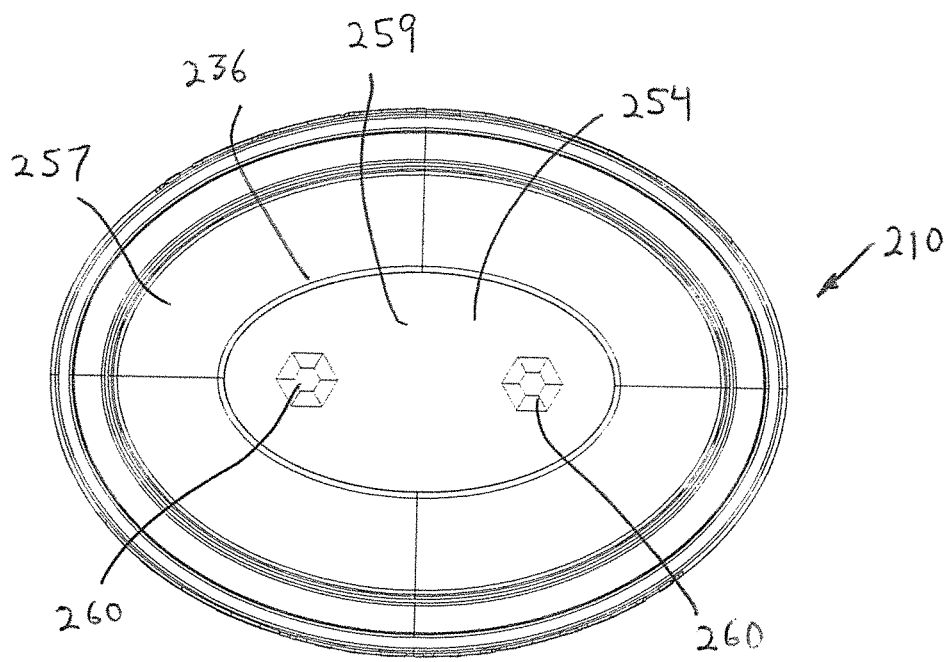
FIG. 46 is a top plan view of the rigid support of FIG. 42.
Figure 47:
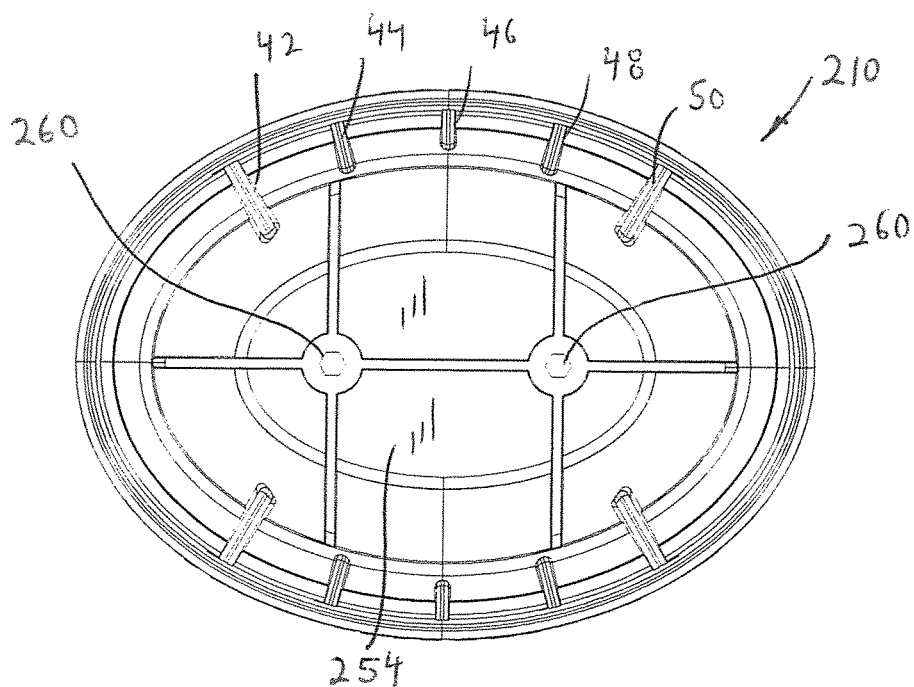
FIG. 47 is a bottom plan view of the rigid support of FIG. 42.
Figure 48:
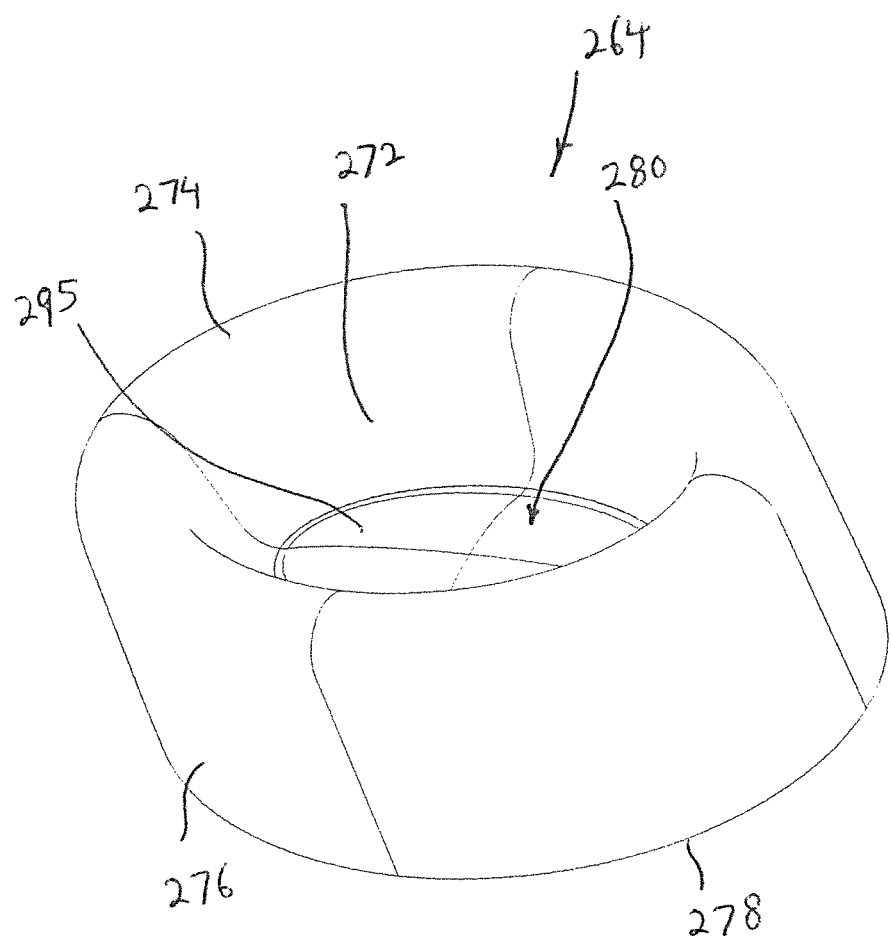
FIG. 48 is a top perspective view of the diaphragm of the applicator of FIG. 36.
Figure 49:
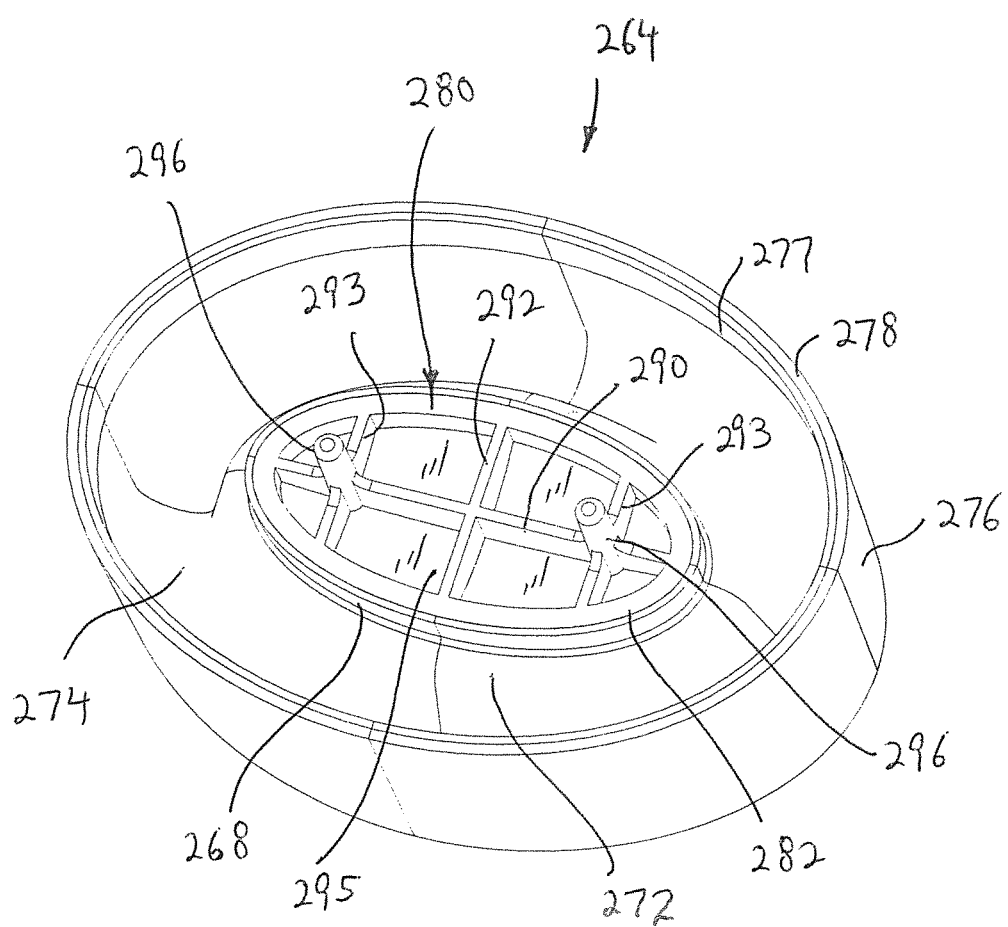
FIG. 49 is a bottom perspective view of the diaphragm of FIG. 48.
Figure 50:
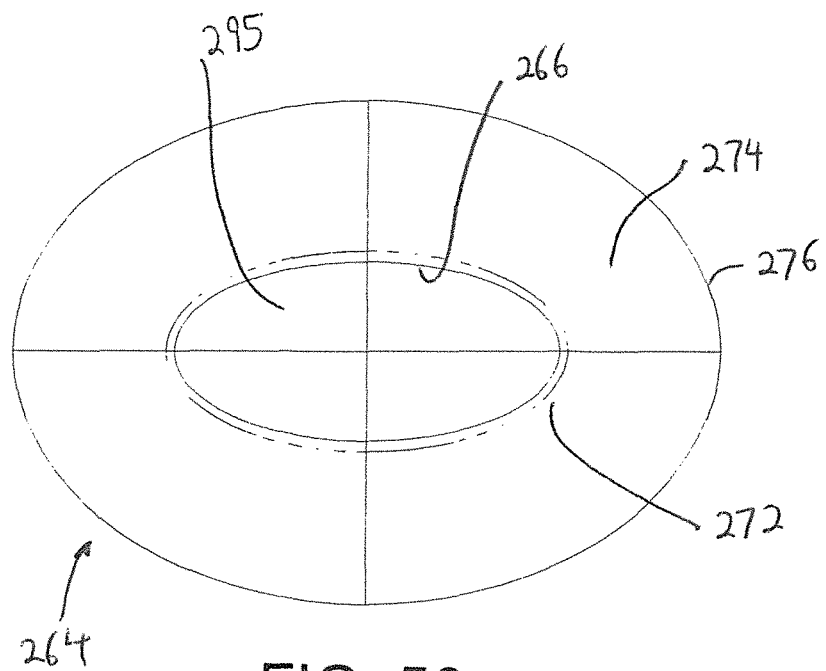
FIG. 50 is a top plan view of the diaphragm of FIG. 48.
Figure 51:
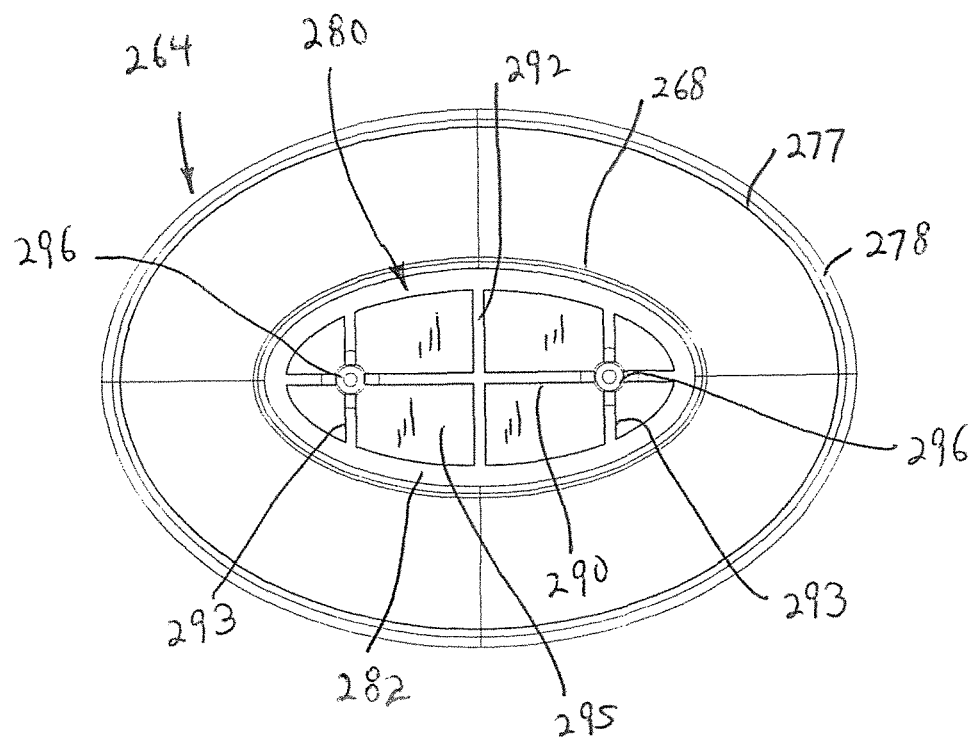
FIG. 51 is a bottom plan view of the diaphragm of FIG. 48, together with a diaphragm holder.

Lastly, when not in use, a cap 114 is provided for covering membrane 64. Specifically, as best shown in FIGS. 34-35, cap 114 includes a thin-walled oval section 116 which is open at its lower end and which is closed by an oval top wall 118 at its upper end. Thin-walled oval section 116 includes four equiangularly spaced elongated beads 120 at the inner surface thereof immediately adjacent the lower open end, for engaging in the four equiangularly spaced elongated depressions 35 of intermediate section 34, so as to releasably lock cap 112 onto intermediate section 34 when applicator 10 is not in use. At such time, the lower edge of thin-walled oval section 116 rests on oval shoulder 38.

A kit can be provided comprising applicator 10, bottle 12 and cap 114. In operation, when used to apply a fluid to a skin surface, applicator 10 is removed from bottle 12 and cap 114 is removed from intermediate section 34. Thereafter, a dose of fluid from bottle 12 is pumped into reservoir 103 by pump 28. Holding support 30, upper folded end 74 of membrane 64 is then placed in contact with the skin surface, causing lower end 78 to move distally down upper section 36 of support 30 towards middle section 34, thereby creating a seal (preferably a vacuum) between membrane 64 and the skin surface. Upper folded end 74 may then be moved across the skin surface by the user until the desired amount of fluid has been applied from the reservoir to the skin.

If the fluid contains a medicament, reservoir 103 can be washed after use to reduce the likelihood of interpersonal transfer of the medicament. The medicated fluid can contain any physiologically active agent which can be delivered to the skin to achieve a desired effect. Thus, the applicator may be used to apply drugs, vitamins, cosmetics, sunscreens, and the like. The medicated fluid may also contain one or more inactive agents, including any one or more of carriers, thickening agents, volatile agents, penetration enhancers, pH adjusting agents, preservatives, surfactants, occlusive agents, emulsifiers, colorants, and the like.

In a particular embodiment, applicator 10 is used to apply a topical or transdermal testosterone composition to the skin of a human in need thereof. Any composition capable of delivering testosterone through the skin can be used and are well known in the art. Any condition can be treated wherein an increase in blood testosterone levels is desired. In an embodiment, the topical or transdermal testosterone composition is applied to one or more axilla of a male in need of testosterone replacement therapy. Conditions associated with deficiency or absence of endogenous testosterone amenable to treatment with a liquid testosterone composition include primary hypogonadism (congenital or acquired), including testicular failure due to conditions such as cryptorchidism, bilateral torsion, orchitis, vanishing testis syndrome, orchiectomy, Klinefelter's syndrome, chemotherapy, or toxic damage from alcohol or heavy metals, and hypogonadotropic hypogonadism (congenital or acquired), including idiopathic gonadotropin or luteinizing hormone-releasing hormone (LHRH) deficiency or pituitary-hypothalamic injury from tumors, trauma, or radiation. The topical or transdermal testosterone composition is preferably capable of maintaining serum testosterone concentrations in the normal range (i.e., approximately 300 ng/dL to about 1050 ng/dL) following one or more applications.

Referring now to FIGS. 36-54, there is shown a modified applicator 210 according to another embodiment of the present invention in which like parts are represented by the same numerals as the first embodiment and modified parts are identified by the same numerals but augmented by 200. As will be discussed hereafter, diaphragm holder 280 is incorporated into membrane 264.

As shown best in FIGS. 36-41 and 48-51, thin-walled membrane or diaphragm 264, in embodiments made of a silicone rubber material, but not limited thereto, has a central opening 266 of an oval shape, with a thin downwardly extending wall 268 formed at the inner periphery of central opening 266 which extends below central opening 266. Oval lip 67, oval shaped ring 68, shallow oval recess and in-turned nubs 70 are eliminated. From the upper end of thin downwardly extending wall 268, that is, from central opening 266, membrane 264 continues upwardly along an inner wall section 272, is folded over at its upper end to form an upper folded end 274 and then continues downwardly to form an outer wall section 276. Lower end 278 of outer wall section 276 is thickened to form an oval shaped stiffener section 277 extending inwardly from lower end 278. However, unlike the free end of the outer wall section of the implement of U.S. Pat. No. 8,177,449 to Bayly et al., which is fixed to the implement, the lower end 278 of outer wall section 276 according to the present invention is not fixed to support 230, and in fact, is free to move axially relative to upper section 236 during application of the fluid to the surface.

Thin downwardly extending wall 268 is fixedly secured to the outer peripheral surface of a membrane or diaphragm holder 280, and particularly, to the outer peripheral surface of a generally oval shaped ring 282 thereof by an adhesive so as to provide a sealing fit therewith. A long rib 290 extends between opposite sides of oval ring 282 along the long axis thereof and a short rib 292 extends between opposite sides of oval ring 282 along the short axis thereof. In addition, other transverse ribs 293 extend in parallel, spaced apart relation to short rib 292 between opposite sides of oval ring 282. A top wall 295 closes the upper end of oval shaped ring 282, and all ribs 290, 292 and 293 are also connected to top wall 295. Central boss 94 of the first embodiment is eliminated. Two guide pins 296 extend down from opposite ends of long rib 290 at the connection of ribs 290 and 293.

In addition, as shown best in FIGS. 42-47, upper section 236 of rigid support 230 is modified. Specifically, the upper edge of upper section 236 is closed off by an upper oval shaped top wall 254, but vent openings and central securing opening 62 are eliminated. Guide openings 260 are provided to receive guide pins 296 with a tight friction and sealing fit to secure membrane 264 to upper section 236. Alternatively, and/or in addition thereto, guide pins 296 can be adhesively secured in guide openings 260. Top wall 254 has lesser dimensions than top wall 54 of the first embodiment, and in this regard, an oval raised wall 255 of a small height extends upwardly from the outer periphery of top wall 254 and an oval ring wall 257 connects the outer periphery of oval raised wall 255 and the upper edge of the side wall of upper section 236. As a result, top wall 254 and oval raised wall 255 form an oval recessed area 259 which receives thin downwardly extending wall 268 of membrane 264 and oval shaped ring 282 of diaphragm holder 280.

Figure 52:
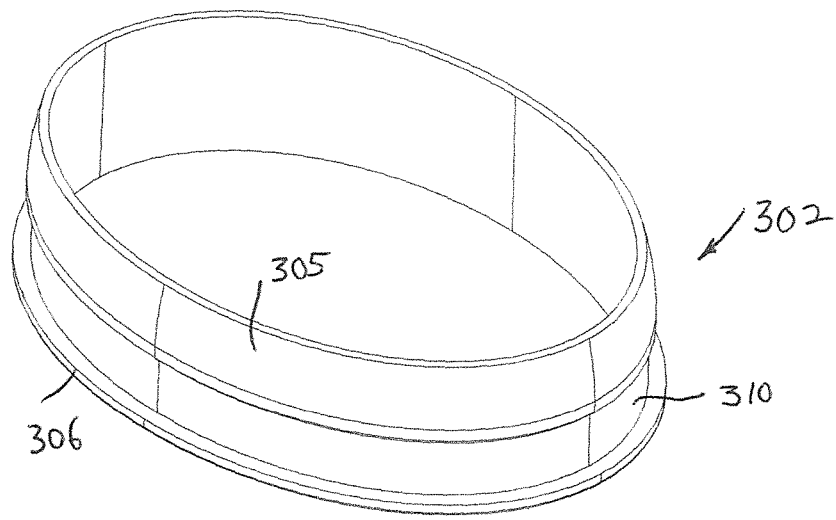
FIG. 52 is a top perspective view of the skirt of the applicator of FIG. 36.
Figure 53:
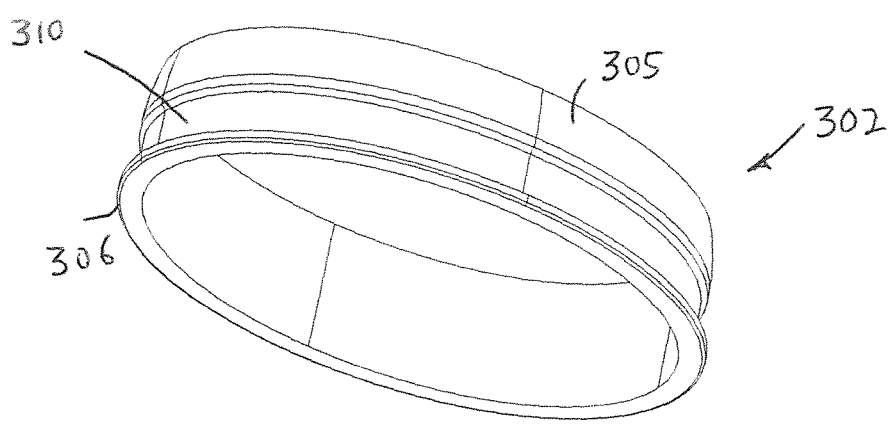
FIG. 53 is a bottom perspective view of the skirt of FIG. 52.
Figure 54:
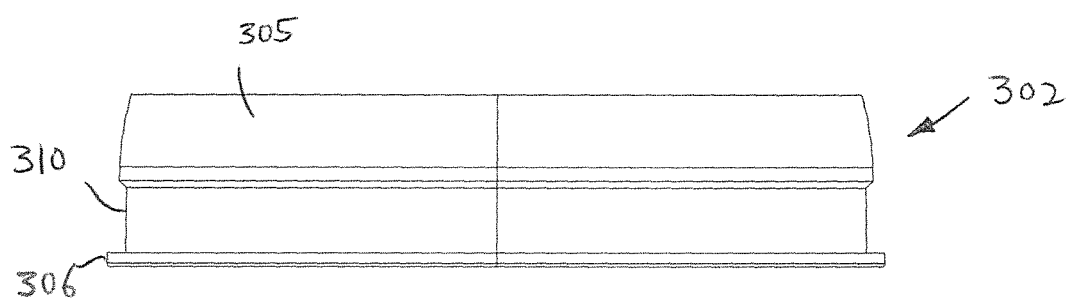
FIG. 54 is a front elevational view of the skirt of FIG. 52.

In order to better provide for controlled free sliding movement of lower end 278 of outer wall section 276, in a preferred embodiment best shown in FIGS. 52-54, lower end 278 is fixed over a skirt 302 formed by an oval shape ring wall 305 having an outwardly extending lower ledge or plate 306 at the lower edge thereof, and an oval recessed area 310 in the outer surface of ring wall 305, extending from a position from lower ledge 306 to a position about halfway up ring wall 305. The lower end of outer wall section 276 is stretch fit over skirt 302, with oval shaped stiffener section 277 fit within oval recessed area 310. The inner dimensions of ring wall 305 are larger than the outer dimensions of upper section 236 so that it can slide up and down relative to upper section 236.

The operation of the modified applicator 210 is the same as the first applicator 10 described above.

It will be appreciated that modifications to the present invention can be made to the scope of the present invention as defined by the appended claims. Thus, for example, while many parts have been described as having an oval shape, the present invention is not limited thereby, and any other suitable shape can be used. In particular, generally circular, square, and rectangular shapes are useful.

Having described certain specific aspects and embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. An applicator for applying a fluid to a surface, the applicator comprising:
    1) a thin-walled, rigid support comprising three thin-walled sections, a lower section, an intermediate section, and an upper section connected to each other in succession;
    2) a flexible membrane comprising a central opening, an inner wall comprising a lower end and an upper end, an outer wall at least partially surrounding an upper outer surface of the support, the outer wall comprising a lower end and an upper end, and an upper folded wall connecting the upper ends of the inner wall and outer wall; and
    3) a membrane holder for fixedly securing the lower end of the inner wall of the flexible membrane to the upper section of the support;
    wherein an upper surface of the membrane holder and the inner wall of the flexible membrane define a reservoir for holding a fluid.

2. The applicator of claim 1, wherein the lower end of the outer wall of the flexible membrane is free to move axially relative to the upper section of the support when pressure is applied to the upper folded wall of the flexible membrane.

3. The applicator of claim 1, wherein the support is open at a lower end thereof adapted to removably mount on a dispenser bottle containing a fluid.

4. The applicator of claim 1, wherein the support is adapted to engage a cap to cover the flexible membrane.

5. The applicator of claim 1, wherein the membrane holder covers and closes the central opening of the flexible membrane.

6. The applicator of claim 1, wherein the upper folded wall of the flexible membrane deforms around its perimeter along an axis that is transverse to the central opening when pressure is applied to the upper folded wall.

7. The applicator according to claim 6, wherein a vacuum seal is formed when pressure is applied to the upper folded wall against a solid or semi-solid surface.

8. The applicator of claim 1, further comprising a skirt secured to the lower end of the outer wall of the flexible membrane, the skirt having dimensions larger than outer dimensions of the upper section of the support for freely moving axially relative to the upper section of the support when pressure is applied to the upper folded wall of the flexible membrane.

9. A method of treating a deficiency of endogenous testosterone in a patient in need thereof, the method comprising providing the applicator of claim 1, placing a testosterone composition in the applicator, and applying the testosterone composition from the applicator to skin of the patient.

10. The method of claim 9, wherein the deficiency of testosterone is the result of a condition selected from the group consisting of primary hypogonadism and hypogonadotropic hypogonadism.

11. The method of claim 10, wherein the primary hypogonadism is testicular failure from a condition selected from the group consisting of cryptorchidism, bilateral torsion, orchitis, vanishing testis syndrome, orchiectomy, Klinefelter's syndrome, chemotherapy, or toxic damage from alcohol or heavy metals.

12. The method of claim 10, wherein the hypogonadotropic hypogonadism is selected from the group consisting of idiopathic gonadotropin deficiency, luteinizing hormone-releasing hormone (LHRH) deficiency, or pituitary-hypothalmic injury from tumors, trauma, or radiation.

13. The method of claim 9, wherein the patient is a male.

14. The method of claim 9, wherein the testosterone composition is a topical or transdermal testosterone composition.

15. The method of claim 14, wherein the topical or transdermal testosterone composition maintains a serum testosterone concentration in the patient in the range of about 300 ng/dL to about 1050 ng/dL.

16. The method of claim 9, wherein the testosterone composition is applied to one or more axilla of the patient.

17. A kit comprising:
    the applicator of claim 1;
    a dispenser bottle containing a testosterone composition; and
    a cap adapted to engage the support and cover the flexible membrane of the applicator.

18. The kit of claim 17, wherein the testosterone composition is a topical or transdermal testosterone composition.

19. The kit of claim 17, wherein the applicator further comprises a skirt secured to the lower end of the outer wall of the flexible membrane, the skirt having dimensions larger than outer dimensions of the upper section of the support for freely moving axially relative to the upper section of the support when pressure is applied to the upper folded wall of the flexible membrane.

* * * * *